United States Patent
Ishiwata et al.

(10) Patent No.: US 6,828,316 B2
(45) Date of Patent: Dec. 7, 2004

(54) DIAMIDE COMPOUND AND MEDICINE CONTAINING THE SAME

(75) Inventors: Hiroyuki Ishiwata, Ichikawa (JP); Mototsugu Kabeya, Higashimurayama (JP); Hiromichi Shigyo, Fuchu (JP); Masami Shiratsuchi, Musashimurayama (JP); Yukio Hattori, Ushiku (JP); Hiroshi Nakao, Tsuchiura (JP); Takao Nagoya, Tsuchiura (JP); Seiichi Sato, Tokyo (JP); Soichi Oda, Higashimurayama (JP); Makoto Suda, Tsukuba (JP); Manabu Shibasaki, Tsukuba (JP)

(73) Assignee: Kowa Co., Ltd., Nagoya (JP)

( * ) Notice: Subject to any disclaimer, the term of this patent is extended or adjusted under 35 U.S.C. 154(b) by 109 days.

(21) Appl. No.: 09/978,102

(22) Filed: Oct. 17, 2001

(65) Prior Publication Data

US 2002/0042414 A1 Apr. 11, 2002

Related U.S. Application Data

(62) Division of application No. 09/147,711, filed as application No. PCT/JP97/02882 on Aug. 20, 1997, now Pat. No. 6,340,682.

(30) Foreign Application Priority Data

Aug. 23, 1996 (JP) .............................................. 8-222770

(51) Int. Cl.[7] ........................ A61K 31/55; A61P 37/00; C07D 243/08
(52) U.S. Cl. ....................................... 514/218; 540/575
(58) Field of Search .......................... 514/718; 540/575

(56) References Cited

U.S. PATENT DOCUMENTS

| | | | |
|---|---|---|---|
| 4,673,684 A | 6/1987 | Wakabayashi et al. | 514/327 |
| 4,917,896 A | 4/1990 | Peck et al. | 514/947 |
| 5,073,544 A | 12/1991 | Peck et al. | 514/24 |

FOREIGN PATENT DOCUMENTS

| | | |
|---|---|---|
| JP | 57-32255 | 2/1982 |
| JP | 1-106818 | 4/1989 |
| JP | 7-17506 | 3/1995 |
| JP | 8-92216 | 4/1996 |

OTHER PUBLICATIONS

N. Matsuura, et al., "An Immunopharmacological Study of (±)–[2–[4–(3–Ethoxy–2–Hydroxypropoxy) Phenylcarbamoyl] Ethyl] Dimethylsulfonium ρ–Toluenesulfonate (Suplatast Tosilate, IPD–1151T) –1. Effect of IPD–1151T on IGE Antibody Formation in Mice and Rats–", *Japan Pharmacol. Ther.*, 1994, vol. 22, No. 3, pp. 265(1369)–279(1383).

U.S. patent application Ser. No. 09/622,586, filed Aug. 21, 2000, pending.

U.S. patent application Ser. No. 09/858,592, filed May 17, 2001, pending.

U.S. patent application Ser. No. 09/978,102, filed Oct. 17, 2001, pending.

*Primary Examiner*—Brenda Coleman
(74) *Attorney, Agent, or Firm*—Oblon, Spivak, McClelland, Maier & Neustadt, P.C.

(57) ABSTRACT

The present invention relates to diamide derivatives represented by the following general formula (1):

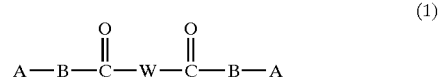

wherein A is a phenyl group or the like, which may be substituted, B is —CH═CH—, —C≡C—, —(CH═CH)₂—, —C≡C—CH═CH—, —CH═CH—C≡C—, phenylene or the like, and W is

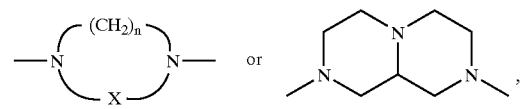

and medicines comprising such a compound. These compounds have an excellent inhibitory effect on the production of an IgE antibody and are hence useful as antiallergic agents and the like.

32 Claims, No Drawings

DIAMIDE COMPOUND AND MEDICINE CONTAINING THE SAME

CROSS-REFERENCE TO RELATED APPLICATIONS

This application is a divisional of application Ser. No. 09/147,711 filed Feb. 23, 1999, now U.S. Pat. No. 6,340,682 which is a national stage entry under 35 U.S.C. § 371 of PCT/JP97/02882, filed Aug. 20, 1997. This application also claims priority to JAPAN 8-222770, filed Aug. 23, 1996.

FIELD OF INVENTION

The present invention relates to novel diamide compounds and medicines useful in preventing and treating allergic immunological diseases, comprising such a compound as an active ingredient.

DESCRIPTION OF THE BACKGROUND

IgE, which is a kind of immunoglobulin (Ig), is an allergen-specific molecule produced by an IgE producing cell differentiated from a B cell. This process is triggered by the contact of an immunocyte with an allergen in vivo.

IgE is produced in a target organ for an allergy and binds to a receptor on the surface of a mast cell, which is a central effector cell in an allergic reaction (sensitized state), or basophil. After the sensitization, allergic chemical mediators such as histamine, leukotrienes, prostaglandins and PAF, and injuring enzymes such as triptase are released from the mast cell stimulated by the reaction of the specific IgE and the allergen which invades in the living body, so that immediate responses, such as vascular permeability acceleration, smooth muscle constriction, and vasodilation are elicited. Further, cytokines such as IL-4, which directly activate other immune system cells, are also secreted from the stimulated mast cell. As a result, eosinophils, basophils and the like infiltrate into a tissue, and the allergic chemical mediators and tissue injuring proteins such as MBP, which are secreted by these inflammatory cells, induce a late response, so that the allergic symptom is lingered and taken seriously ill.

From this, IgE is considered a substance fundamentally participating in the attack of an allergic immunological disease.

Therefore, several compounds having an inhibitory effect on the production of an IgE antibody have been found and reported to date with a view toward developing antiallergic agents [Pharmacology and Therapy, 1994, 22(3), 1369; Japanese Patent Application Laid-Open No. 106818/1989; Japanese Patent Publication No. 17506/1995; and Japanese Patent Application Laid-Open No. 92216/1996]. However, the object has been not always sufficiently achieved under the circumstances.

SUMMARY OF THE INVENTION

Accordingly, it is an object of the present invention to find a compound having a strong inhibitory effect on the production of an IgE antibody so as to provide a medicine effective for allergic immunological diseases, comprising this compound as an active ingredient.

DETAILED DISCLOSURE OF THE PREFERED EMBODIMENT

With the foregoing circumstances in view, the present inventors have carried out an extensive investigation. As a result, it has been found that novel diamide compounds represented by the general formula (1), which will be described subsequently, salts thereof, or hydrates or solvates thereof have an excellent inhibitory effect on the production of an IgE antibody and are useful for medicines such as antiallergic agents, thus leading to completion of the present invention.

According to the present invention, there is thus provided a compound represented by the following general formula (1):

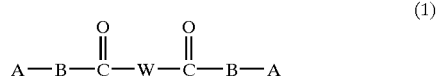

wherein A is a phenyl, naphthyl, dihydronaphthyl, indenyl, pyridyl, indolyl, isoindolyl, quinolyl or isoquinolyl group which may be substituted;

B is a group of —CH=CH—, —C≡C—, —(CH=CH)$_2$—, —CH=CH—C≡C— or —C≡C—CH=CH—, or a divalent residue of benzene, pyridine, pyrimidine or pyrazine; and W is a formula

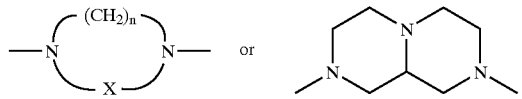

in which X is

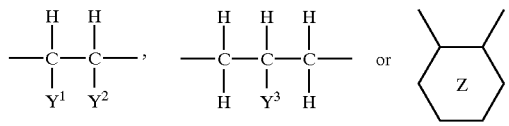

($Y^1$, $Y^2$ and $Y^3$ are the same or different from one another and are independently a hydrogen atom, —COOR$^1$ (R$^1$ is a hydrogen atom or a lower alkyl group), —CON(R$^2$)R$^3$ (R$^2$ and R$^3$ are the same or different from each other and are independently a hydrogen atom, or a hydroxyl or lower alkyl group), —CH$_2$—N(R$^4$)R$^5$ (R$^4$ and R$^5$ are the same or different from each other and are independently a hydrogen atom or a lower alkyl group, or R$^4$ and R$^5$ may form, together with the adjacent nitrogen atom, a heterocyclic ring which may further have an oxygen, nitrogen or sulfur atom), or —CH$_2$—S—R$^6$ (R$^6$ is a lower alkyl, phenyl or pyridyl group), or $Y^1$ and $Y^2$ may couple to each other to form an alkylene group which may be through an oxygen, a nitrogen or a sulfur, Z is a benzene or pyridine ring, and n is an integer of 2 or 3, with the proviso that when B is a p-phenylene group, and W is a 1,4-piperazinyl group, A is not a phenyl group, and when B is —CH=CH—, A is not a phenyl group which may be substituted, or a salt thereof, or a hydrate or solvate thereof.

According to the present invention, there is also provided a medicine comprising the above compound as an active ingredient.

According to the present invention, there is further provided a medicinal composition comprising the above compound and a pharmaceutically acceptable carrier.

According to the present invention, there is still further provided use of the above compound for a medicine.

According to the present invention, there is yet still further provided a method of treating an allergic immunological disease, which comprises administering an effective amount of the above compound.

BEST MODE FOR CARRYING OUT THE INVENTION

The amide compounds according to the present invention are represented by the general formula (1). In these compounds, the lower alkyl groups include linear or branched alkyl groups having 1–8 carbon atoms. Specific examples thereof include methyl, ethyl, n-propyl, i-propyl, n-butyl, i-butyl, sec-butyl, tert-butyl, pentyl, hexyl, heptyl and octyl groups. Of these, those having 1–6 carbon atoms, for example, methyl, ethyl, propyl, i-propyl, n-butyl, i-butyl, tert-butyl, n-pentyl and n-hexyl groups, are particularly preferred.

The lower alkoxy groups include linear or branched alkoxy groups having 1–8 carbon atoms. Specific examples thereof include methoxy, ethoxy, n-propoxy, i-propoxy, n-butoxy, i-butoxy, sec-butoxy, tert-butoxy, pentyloxy, hexyloxy, heptyloxy and octyloxy groups. Of these alkoxy groups, those having 1–6 carbon atoms are preferred.

The halogen atoms include fluorine, chlorine, bromine and iodine atoms.

In the formula (1), A is a phenyl, naphthyl, dihydronaphthyl, indenyl, pyridyl, indolyl, i-indolyl, quinolyl or i-quinolyl group. These groups may have 1–3 substituents. Here, examples of the substituents on these groups include a hydroxyl group, halogen atoms, lower alkyl groups which may be substituted by 1–3 halogen atoms, lower alkoxy groups, an amino group which may be substituted by one or two lower alkyl groups, and alkylthio groups.

Particularly preferable examples of A include tri-lower alkoxy-phenyl groups.

In B, examples of the substituent on the divalent residue of benzene, pyridine, pyrimidine or pyrazine include nitro, amino, lower alkyl and lower alkoxy groups, and halogen atoms.

More preferred as B is —CH=CH—, —C≡C—, —(CH=CH)$_2$—, —C≡C—CH=CH—, —CH=CH—C≡C—, or a divalent residue of benzene, pyridine, pyrimidine or pyrazine. Of these, —CH=CH—CH=CH—, —C≡C—CH=CH—, —CH=CH—C≡C— and a benzene residue (phenylene group) are particularly preferred.

In the general formula (1), preferable example of the heterocyclic ring which is formed by R$^4$ and R$^5$ together with the adjacent nitrogen atom include those having 3–10 carbon atoms. Specific examples thereof include pyrrolidine, oxazole, isoxazole, thiazole, isothiazole, imidazole, imidazoline, imidazolidine, pyridine, piperidine, piperazine, morpholine and phthalimide. The alkylene group formed by bonding Y$^1$ and Y$^2$ to each other preferably has 3–8 carbon atoms. Rings formed by the alkylene group which may be through an oxygen, a nitrogen or a sulfur include pyrrolidine, imidazolidine and piperazine. More preferred as Y$^1$, Y$^2$ and Y$^3$ are a hydrogen atom, and carboxyl, aminomethyl, di-lower alkyl-amino and lower alkyl-aminomethyl groups, with a hydrogen atom, and carboxyl, aminomethyl, dimethylamino and dimethylaminomethyl groups being particularly preferred.

Particularly preferred as W is piperazine or homopiperazine ring which may be substituted by a carboxyl, aminomethyl, di-lower alkyl-amino or di-lower alkyl-aminomethyl group, or

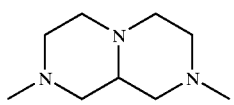

Incidentally, in the general formula (1), A is not a phenyl group when B is a p-phenylene group, and W is a 1,4- piperazinyl group. A is not a phenyl group which may be substituted when B is —CH—CH—.

The salts of the diamide compounds (1) may be any salts so far as they are pharmaceutically acceptable salts. Examples thereof include mineral acid salts such as sulfates; organic acid salts such as methanesulfonates, acetates, oxalates and citrates, and besides in the case where the diamide compounds (1) are acidic compounds, alkali metal salts such as sodium salts and potassium salts; alkaline earth metal salts such as calcium salts and magnesium salts; and organic basic salts such as pyridine salts, picoline salts and triethylamine salts.

The diamide compounds (1) may also be present in the form of a solvate.

The diamide compounds (1) can be prepared in accordance with, for example, the following reaction formula:

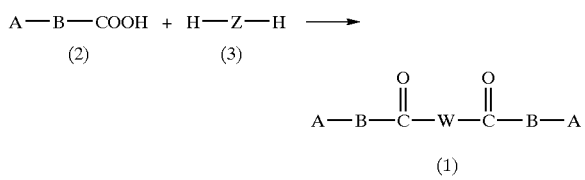

More specifically, the compounds (1) according to the present invention are obtained by the N-acylating reaction of a carboxylic acid (2) or a reactive derivative thereof with an amine (3).

The N-acylating reaction may be conducted by using any N-acylating reaction known per se in the art. It is particularly preferable to apply, for example, (a) a method in which the carboxylic acid (2) and the amine (3) are reacted in the presence of a base and/or a condensation agent in a solvent, or (b) a method in which a reactive derivative of the carboxylic acid (2) and the amine (3) are reacted in a solvent.

Examples of the solvents used in these reactions may include dimethylformamide, tetrahydrofuran, dioxane, acetonitrile, methylene chloride and dichloroethane. Examples of the base may include organic bases such as pyridine, triethylamine and diisopropylethylamine, and inorganic bases such as sodium carbonate and sodium hydrogencarbonate. Examples of usable condensation agents include 1,3-dicyclohexylcarbodiimide, 1-cyclohexyl-3-morpholinoethylcarbodiimide, 1-(3-dimethylaminopropyl)-3-ethylcarbodiimide, 1,1'-carbonyldiimidazole, diethyl phosphorocyanidate, diphenylphosphoryl azide, bis(2-oxo-3-oxazolidinyl)phosphinic chloride and 2-chloro-1-methylpyridinium iodide. Examples of usable derivatives of the carboxylic acid include acid halides such as acid chlorides, acid azides, symmetric acid anhydrides, mixed anhydrides with pivalic acid or the like, and active esters such as cyanomethyl esters and p-nitrophenyl esters.

In each of the method (a) and the method (b), the N-acylating reaction is completed by reacting the carboxylic acid (2) or the reactive derivative thereof with the amine (3) at a reaction temperature of 0° C. to 100° C. for 30 minutes to 30 hours. The isolation and purification of the compound (1) from the reaction mixture may be conducted by using any methods known per se in the art, for example, filtration, extraction, washing, drying, concentration, recrystallization and various kinds of chromatography.

The compound (1) thus obtained may be converted into an acid-addition salt in a method known per se in the art.

The compound may also be converted into a solvate with a solvent for reaction, a solvent for recrystallization, or the like, in particular, a hydrate.

Since the diamide compounds (1) according to the present invention have an excellent inhibitory effect on the production of an IgE antibody, they are useful as medicines for prevention and treatment of various allergic immunological diseases, in which IgE participates, for example, asthma, atopic dermatitis, allergic rhinitis, inflammatory bowel diseases and contact dermatitis.

The diamide compounds (1) or the salts thereof can be formulated into various oral and parenteral preparations in the form of a solid, semisolid or liquid by adding a pharmaceutically acceptable carrier in accordance with a method known per se in the art.

Examples of the oral preparations include tablets, pills, granules, soft and hard capsules, powders, grains, triturations, emulsions, syrups, pellets and elixirs. Examples of the parenteral preparations include injections, drops, infusions, ointments, lotions, tonics, sprays, inhalation suspensions, oils, emulsions and suppositories. The active ingredients according to the present invention may be formulated into various preparations in accordance with a method known per se in the art. In these preparations, may be used surfactants, excipients, colorants, smell corrigents, preservatives, stabilizers, buffers, suspension stabilizers, isotonic agents and the like, as needed.

The dose of the diamide compound (1) or the salt thereof varies according to the kind of the compound, the kind of a disease to be treated or prevented, an administration method, the condition, age, sex, weight of a patient to be administered, treatment time, and the like. However, the compound may be administered in a dose of 0.01–1,000 mg/kg (weight)/day. The compound may be administered at once or in several portions, for example, 2 to 6 portions a day.

EXAMPLES

The present invention will hereinafter be described in more detail by the following Examples. However, the present invention is not limited to these examples. Referential Example 1:

5-Phenylpenta-(2E,4E)-dienoic acid[1]

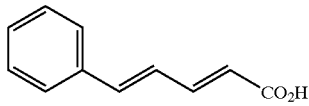

To a solution of 16 ml (72 mmol) of triethyl 4-phosphonocrotonate in anhydrous tetrahydrofuran (100 ml) was added 43 ml (69 mmol) of a 1.6 M n-butyllithium solution dropwise with stirring in an ice-salt bath under nitrogen, and the mixture was stirred for 30 minutes. Then, 5.0 ml (49 mmol) of benzaldehyde was added dropwise to this reaction mixture over about 5 minutes, and the resultant mixture was stirred for 10 minutes in the ice-salt bath and for an additional 3 hours at room temperature. A saturated aqueous solution of ammonium chloride was added to the reaction mixture to conduct extraction with ether. An organic layer was dried over anhydrous sodium sulfate and then concentrated under reduced pressure, and the resultant crude oil (15.9 g) was purified by chromatography on silica gel, thereby obtaining 8.14 g (yield: 82%) of ethyl 5-phenylpenta-(2E,4E)-dienoate.

Added to a solution of 8.14 g (40.3 mmol) of ethyl 5-phenylpenta-(2E,4E)-dienoate synthesized by the above process in methanol-tetrahydrofuran (40 ml–80 ml) was 40 ml of a 5N aqueous solution of potassium hydroxide, and the mixture was stirred for 1 hour at room temperature. The reaction mixture was concentrated under reduced pressure, and the resultant residue was cooled in an ice bath. To it were added 20 ml of chloroform and concentrated hydrochloric acid with vigorous stirring. An aqueous layer and an organic layer were separated from each other, and the aqueous layer was further extracted with chloroform. The resultant organic layers were collected, dried over anhydrous sodium sulfate and then concentrated under reduced pressure. The resultant crude oil was recrystallized from ethyl acetate-hexane to purify it, thereby obtaining 5.91 g (yield: 84%) of the title compound. (1) Saljoughian, M.; Williams, P. G., J. Org. Chem. 1987, 52, 3481–3483.

Example 1

Preparation of 1,4-bis[5-phenylpenta-(2E,4E)-dienoyl]hexahydro-1,4-diazepine:

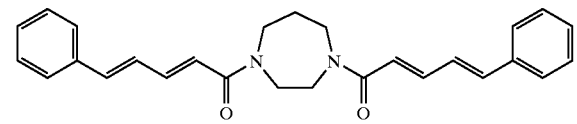

After 2.49 g (14.3 mmol) of 5-phenylpenta-(2E,4E)-dienoic acid were added to a solution of 653 mg (6.51 mmol) of homopiperazine in anhydrous dimethylformamide (30 ml), a reaction vessel was transferred to an ice bath, and 2.7 ml (19 mmol) of triethylamine and 3.0 ml (14 mmol) of diphenylphosphorylazide were added and the resultant mixture was stirred for 1 hour. Added to the reaction mixture was 40 ml of a 5% aqueous solution of sodium hydrogencarbonate to conduct extraction with chloroform. An organic layer was dried over anhydrous sodium sulfate and then concentrated under reduced pressure. The resultant crude oil (8.4 g) was purified by column chromatography on alumina and column chromatography on silica gel, and then recrystallized from ethyl acetate-hexane, thereby obtaining 2.18 g (yield: 81%) of the title compound as a colorless crystalline powder.

Melting point: 155–156° C.

$^1$H-NMR (DMSO-$d_6$, 120° C.) δ:
1.81(tt,J=6.0,6.0 Hz,2H), 3.58(dd,J=6.0,6.0 Hz,4H), 3.70(s,4H), 6.63(d,J=14.6 Hz,2H), 6.90(d,J=15.6 Hz,2H), 7.02(dd,J=15.6,10.3 Hz,2H), 7.23(dd,J=14.6,10.3 Hz,2H),
7.23–7.37(m,6H), 7.44–7.49(m,4H).

Example 2

Preparation of 1,4-bis[5-(2-methoxyphenyl)penta-(2E,4E)-dienoyl]hexahydro-1,4-diazepine:

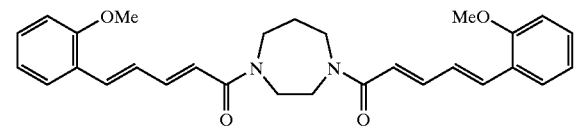

In accordance with the same process as in Example 1, 223 mg (yield: 97%) of the title compound was obtained as a colorless amorphous powder from 200 mg (0.98 mmol) of 5-(2-methoxyphenyl)penta-(2E,4E)-dienoic acid and 49 mg (0.49 mmol) of homopiperazine.

$^1$H-NMR (DMSO-$d_6$, 120° C.) δ:
1.81(tt,J=6.0,6.0 Hz,2H), 3.58(dd,J=6.0,6.0 Hz,4H), 3.68(s,4H), 3.83(s,6H), 6.58(d,J=14.5 Hz,2H), 6.92(ddd,J=7.4,7.4,1.0 Hz,2H), 6.97–7.13(m,4H),
7.00(dd,J=8.4,1.0 Hz,2H),
7.23(ddd,J=14.5,9.0,1.5 Hz,2H),
7.25(ddd,J=8.4,7.4,1.7 Hz,2H), 7.48(dd,J=7.4,1.7 Hz,2H).

Example 3

Preparation of 1,4-bis[5-(3-trifluoromethylphenyl)-penta-(2E,4E)-dienoyl]hexahydro-1,4-diazepine:

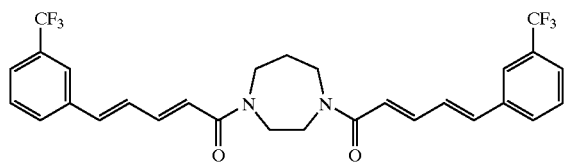

In accordance with the same process as in Example 1, 216 mg (yield: 94%) of crude crystals of the title compound were obtained from 202 mg (0.84 mmol) of 5-(3-trifluoromethylphenyl)penta-(2E,4E)-dienoic acid and 42 mg (0.42 mmol) of homopiperazine. The crude crystals thus obtained were recrystallized from chloroform-hexane, thereby obtaining a colorless crystalline powder.

Melting point: 181–182° C.

$^1$H-NMR (CDCl$_3$) (mixture of amide rotamers) δ:
1.90–2.05(m,2H), 3.56–3.88(m,4H), 3.80(s,4H),
6.48(br d,J=14.5 Hz,1.3H), 6.50(br d,J=14.5 Hz,0.7H),
6.82–7.09(m,4H), 7.40–7.73(m,10H).

Example 4

Preparation of 1,4-bis[5-(3-methoxyphenyl)penta-(2E,4E)-dienoyl]hexahydro-1,4-diazepine:

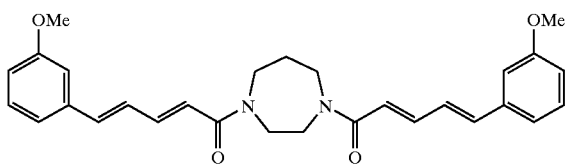

In accordance with the same process as in Example 1, 133 mg (yield: 62%) of the title compound was obtained as a pale yellow amorphous powder from 186 mg (0.91 mmol) of 5-(3-methoxyphenyl)penta-(2E,4E)-dienoic acid and 46 mg (0.46 mmol) of homopiperazine.

$^1$H-NMR (DMSO-d$_6$, 120° C.) δ:
1.81(tt,J=6.0,6.0 Hz,2H), 3.58(dd,J=6.0,6.0 Hz,4H),
3.69(s,4H), 3.78(s,6H), 6.63(d,J=14.8 Hz,2H),
6.85(ddd,J=8.1,2.6,0.9 Hz,2H), 6.87(d,J=15.1 Hz,2H),
7.02(dd,J=15.1,10.5 Hz,2H), 6.99–7.09(m,4H),
7.23(dd,J=14.8,10.5 Hz,2H), 7.24(dd,J=8.1,8.1 Hz,2H).

Example 5

Preparation of 1,4-bis[5-(4-fluorophenyl)penta-(2E,4E)-dienoyl]hexahydro-1,4-diazepine:

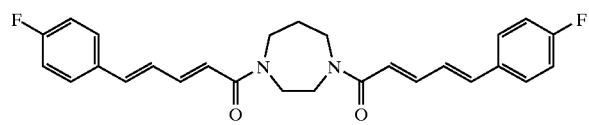

In accordance with the same process as in Example 1, 217 mg (yield: 94%) of the title compound was obtained as a colorless amorphous powder from 202 mg (1.1 mmol) of 5-(4-fluorophenyl)penta-(2E,4E)-dienoic acid and 47 mg (0.47 mmol) of homopiperazine. The amorphous powder thus obtained was recrystallized from methanol-chloroform-hexane, thereby obtaining a colorless crystalline powder.

Melting point: 230–231° C.

$^1$H-NMR (CD$_3$OD-CDCl$_3$) (mixture of amide rotamers) δ:
1.90–2.05(m,2H), 3.55–3.75(m,4H), 3.78(s,4H),
6.43(br d,J=14.5 Hz,1.3H), 6.47(br d,J=14.5 Hz,0.7H),
6.82–6.91(m,4H), 7.06(dd,J=8.7,$^3$J$_{HF}$=8.7 Hz,4H),
7.35–7.55(m,6H).

Example 6

Preparation of 1,4-bis[5-(4-trifluoromethylphenyl)-penta-(2E,4E)-dienoyl]hexahydro-1,4-diazepine:

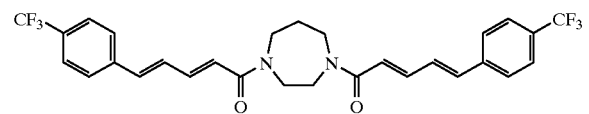

In accordance with the same process as in Example 1, 217 mg (yield: 79%) of the title compound was obtained as a colorless amorphous powder from 242 mg (1.0 mmol) of 5-(4-trifluoromethylphenyl)penta-(2E,4E)-dienoic acid and 51 mg (0.51 mmol) of homopiperazine. The amorphous powder thus obtained was recrystallized from methanol-chloroform-hexane, thereby obtaining colorless needles.

Melting point: 233–235° C.

$^1$H-NMR (CDCl$_3$) (mixture of amide rotamers) δ:
2.00(br tt,J=6.1,6.1 Hz,2H), 3.58–3.82(m,8H),
6.48(d,J=6.7 Hz,1.3H), 6.52(d,J=6.7 Hz,0.7H),
6.84–7.04(m,4H), 7.41–7.64(m,10H).

Example 7

Preparation of 1,4-bis[5-(4-tert-butylphenyl)penta-(2E,4E)-dienoyl]hexahydro-1,4-diazepine:

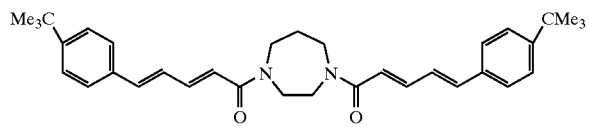

In accordance with the same process as in Example 1, 410 mg (yield: 78%) of the title compound was obtained as a colorless amorphous powder from 460 mg (2.0 mmol) of 5-(4-tert-butylphenyl)penta-(2E,4E)-dienoic acid and 100 mg (1.0 mmol) of homopiperazine. The amorphous powder thus obtained was recrystallized from ethyl acetate-hexane, thereby obtaining colorless needles.

Melting point: 162–164° C.

$^1$H-NMR (CDCl$_3$) (mixture of amide rotamers) δ:
1.32(s,18H), 1.90–2.07(m,2H), 3.58–3.82(m,8H),
6.39(d,J=14.7 Hz,1.3H), 6.42(d,J=14.7 Hz,0.7H),
6.81–6.92(m,4H), 7.29–7.60(m,10H).

Example 8

Preparation of 1,4-bis[(5-(4-chlorophenyl)penta-(2E,4E)-dienoyl]hexahydro-1,4-diazepine:

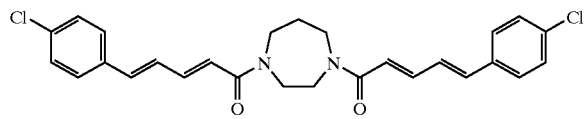

In accordance with the same process as in Example 1, 122 mg (yield: 65%) of the title compound was obtained as a colorless crystalline powder from 197 mg (0.94 mmol) of 5-(4-chlorophenyl)penta-(2E,4E)-dienoic acid and 39 mg (0.39 mmol) of homopiperazine.

Melting point: 248–250° C.

$^1$H-NMR (DMSO-$d_6$, 120° C.) δ:

1.80(tt,J=6.0,6.0 Hz,2H), 3.58(dd,J=6.0,6.0 Hz,4H),
3.69(s,4H), 6.63(d,J=14.6 Hz,2H),
6.88(d,J=15.5 Hz,2H), 7.02(dd,J=15.5,10.4 Hz,2H),
7.21(dd,J=14.6,10.4 Hz,2H), 7.35(d,J=8.6 Hz,4H),
7.48(d,J=8.6 Hz,4H).

Example 9

Preparation of 1,4-bis[5-(4-di-n-butylaminophenyl)-penta-(2E,4E)-dienoyl]hexahydro-1,4-diazepine dihydrochloride:

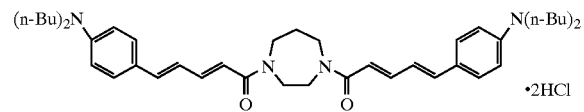

In accordance with the same process as in Example 1, 161 mg (yield: 79%) of 1,4-bis[5-(4-di-n-butylaminophenyl)-penta-(2E,4E)-dienoyl]hexahydro-1,4-diazepine was obtained as a yellow oil from 192 mg (0.64 mmol) of 5-(4-di-n-butylaminophenyl) penta-(2E,4E)-dienoic acid and 31 mg (0.31 mmol) of homopiperazine. Added to a solution of 130 mg of the thus-obtained yellow oil in ethanol (5 ml) was 0.5 ml of 1N hydrochloric acid, and the resultant mixture was concentrated under reduced pressure. Thereafter, ether was added, thereby obtaining the title compound as a yellow amorphous powder.

$^1$H-NMR (DMSO-$d_6$, 120° C.) (mixture of amide rotamers) δ:

0.91(t,J=7.4 Hz,12H), 1.33(tq,J=7.4,7.4 Hz,8H),
1.53(tt,J=7.4,7.4 Hz,8H), 1.80(br tt,J=5.9,5.9 Hz,2H),
3.30(t,J=7.4 Hz,8H), 3.56(br dd,J=5.9,5.9 Hz,4H),
3.67(s,4H), 6.47(d,J=14.7 Hz,2H), 6.70–6.81(m,4H),
6.77(d,J=8.6 Hz,4H), 7.16–7.32(m,2H),
7.32(d,J=8.6 Hz,4H).

Example 10

Preparation of 1,4-bis[5-(4-methoxyphenyl)penta-(2E,4E)-dienoyl]hexahydro-1,4-diazepine:

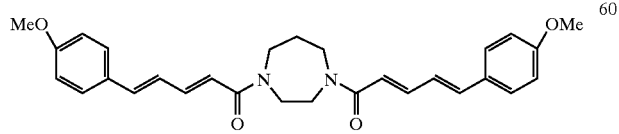

In accordance with the same process as in Example 1, crude crystals were obtained from 200 mg (0.98 mmol) of 5-(4-methoxyphenyl)penta-(2E,4E)-dienoic acid and 49 mg (0.49 mmol) of homopiperazine. The thus-obtained crude crystals were recrystallized from chloroform-hexane, thereby obtaining 213 mg (yield: 92%) of the title compound as a colorless crystalline powder.

Melting point: 210–212° C.

$^1$H-NMR (DMSO-$d_6$, 120° C.) δ:

1.80(tt,J=6.0,6.0 Hz,2H), 3.57(dd,J=6.0,6.0 Hz,4H),
3.68(s,4H), 3.78(s,6H), 6.55(d,J=14.7 Hz,2H),
6.80–6.95(m,4H), 6.90(d,J=8.9 Hz,4H),
7.21(ddd,J=14.7,7.5,2.7 Hz,2H), 7.41(d,J=8.9 Hz,4H).

Example 11

Preparation of 1,4-bis[5-(2,6-dimethoxyphenyl)penta-(2E,4E)-dienoyl]hexahydro-1,4-diazepine:

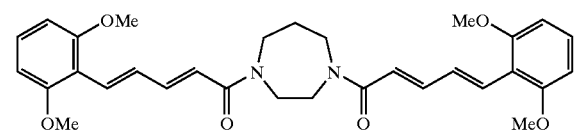

In accordance with the same process as in Example 1, 194 mg (quantitative) of the title compound was obtained as a colorless amorphous powder from 204 mg (0.87 mmol) of 5-(2,6-dimethoxyphenyl)penta-(2E,4E)-dienoic acid and 37 mg (0.37 mmol) of homopiperazine.

$^1$H-NMR (DMSO-$d_6$, 120° C.) 67 :

1.81(tt,J=6.0,6.0 Hz,2H), 3.57(dd,J=6.0,6.0 Hz,4H),
3.68(s,4H), 3.83(s,12H), 6.50(d,J=14.2 Hz,2H),
6.65(d,J=8.4 Hz,4H), 7.07(d,J=15.3 Hz,2H),
7.19(dd,J=14.2,10.6 Hz,2H), 7.20(t,J=8.4 Hz,2H),
7.29(dd,J=15.3,10.6 Hz,2H).

Example 12

Preparation of 1,4-bis[5-(2,4-dimethoxyphenyl)penta-(2E,4E)-dienoyl]hexahydro-1,4-diazepine:

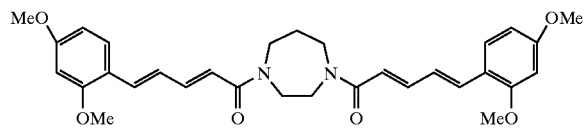

In accordance with the same process as in Example 1, 170 mg (yield: 73%) of the title compound was obtained as a colorless amorphous powder from 206 mg (0.88 mmol) of 5-(2,4-dimethoxyphenyl)penta-(2E,4E)-dienoic acid and 44 mg (0.44 mmol) of homopiperazine.

$^1$H-NMR (DMSO-$d_6$, 120° C.) δ:

1.80(tt,J=5.9,5.9 Hz,2H), 3.56(dd,J=5.9,5.9 Hz,4H),
3.67(s,4H), 3.79(s,6H), 3.83(s,6H),
6.50(d,J=14.6 Hz,2H), 6.52(dd,J=8.5,2.3 Hz,2H),
6.56(d,J=2.3 Hz,2H), 6.90(dd,J=15.6,9.8 Hz,2H),
7.00(d,J=15.6 Hz,2H), 7.20(dd,J=14.6,9.8 Hz,2H),
7.40(d,J=8.5 Hz,2H).

Example 13

Preparation of 1,4-bis[5-(4-tert-butyl-2-methoxy-phenyl)penta-(2E,4E)-dienoyl]hexahydro-1,4-diazepine:

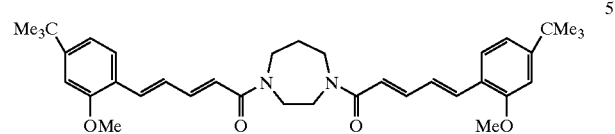

In accordance with the same process as in Example 1, 238 mg (yield: 91%) of the title compound was obtained as a pale yellow amorphous powder from 234 mg (0.90 mmol) of 5-(4-tert-butyl-2-methoxyphenyl)penta-(2E,4E)-dienoic acid and 45 mg (0.45 mmol) of homopiperazine.

$^1$H-NMR (DMSO-$d_6$, 120° C.) δ:

1.30(s,18H), 1.80(tt,J=6.0,6.0 Hz,2H),
3.57(dd,J=6.0,6.0 Hz,4H), 3.68(s,4H), 3.84(s,6H),
6.55(d,J=14.5 Hz,2H), 6.93–7.12(m,8H),
7.22(ddd,J=14.5,8.6,1.6 Hz,2H), 7.40(d,J=7.8 Hz,2H).

Example 14

Preparation of 1,4-bis[5-(3,4-dimethoxyphenyl)penta-(2E,4E)-dienoyl]hexahydro-1,4-diazepine:

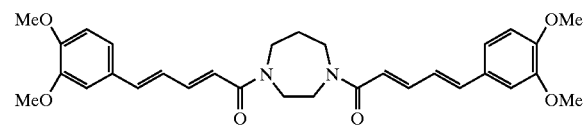

In accordance with the same process as in Example 1, 182 mg (yield: 83%) of the title compound was obtained as a colorless amorphous powder from 217 mg (0.82 mmol) of 5-(3,4-dimethoxyphenyl)penta-(2E,4E)-dienoic acid and 41 mg (0.41 mmol) of homopiperazine.

$^1$H-NMR (DMSO-$d_6$, 120° C.) δ:

1.81(tt,J=5.8,5.8 Hz,2H), 3.58(dd,J=5.8,5.8 Hz,4H),
3.68(s,4H), 3.78(s,6H), 3.80(s,6H),
6.55(d,J=14.6 Hz,2H), 6.81(d,J=15.8 Hz,2H),
6.91(dd,J=15.8,9.9 Hz,2H), 6.91(d,J=8.4 Hz,2H),
7.02(dd,J=8.4,2.1 Hz,2H), 7.10(d,J=2.1 Hz,2H),
7.21(dd,J=14.6,9.9 Hz,2H).

Example 15

Preparation of 1,4-bis[5-(3,5-dimethoxyphenyl)penta-(2E,4E)-dienoyl]hexahydro-1,4-diazepine:

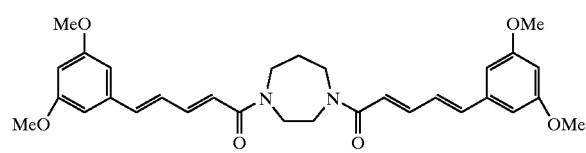

In accordance with the same process as in Example 1, 186 mg (yield: 95%) of the title compound was obtained as a colorless amorphous powder from 207 mg (0.83 mmol) of 5-(3,5-dimethoxyphenyl)penta-(2E,4E)-dienoic acid and 37 mg (0.37 mmol) of homopiperazine.

$^1$H-NMR (DMSO-$d_6$, 120° C.) δ:

1.81(tt,J=6.0,6.0 Hz,2H), 3.58(dd,J=6.0,6.0 Hz,4H),
3.68(s,4H), 3.76(s,12H), 6.43(t,J=2.2 Hz,2H),
6.63(d,J=14.5 Hz,2H), 6.65(d,J=2.2 Hz,4H),
6.82(d,J=15.4 Hz,2H), 7.01(dd,J=15.4,10.7 Hz,2H),
7.21(dd,J=14.5,10.7 Hz,2H).

Example 16

Preparation of 1,4-bis[5-(2,4,6-trimethoxyphenyl)-penta-(2E,4E)-dienoyl]hexahydro-1,4-diazepine:

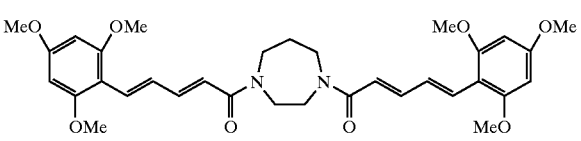

In accordance with the same process as in Example 1, crude crystals were obtained from 211 mg (0.80 mmol) of 5-(2,4,6-trimethoxyphenyl)penta-(2E,4E)-dienoic acid and 41 mg (0.41 mmol) of homopiperazine. The crude crystals were recrystallized from ethanol-ether, thereby obtaining 177 mg (yield: 75%) of the title compound as a pale yellow crystalline powder.

Melting point: 190–195° C.

$^1$H-NMR (DMSO-$d_6$, 120° C.) (mixture of amide rotamers) δ:

1.80(br tt,J=6.0,6.0 Hz,2H),
3.56(br dd,J=6.0,6.0 Hz,4H), 3.66(br s,4H), 3.80(s,6H),
3.82(s,12H), 6.24(s,4H), 6.36–6.47(m,2H),
6.94–7.07(m,2H), 7.10–7.24(m,4H).

Example 17

Preparation of 1,4-bis[5-(3,4,5-trimethoxyphenyl)-penta-(2E,4E)-dienoyl]hexahydro-1,4-diazepine:

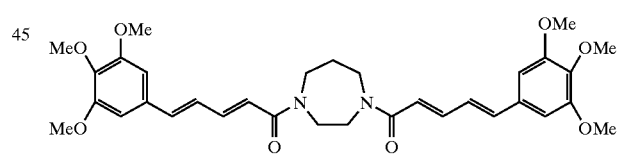

In accordance with the same process as in Example 1, crude crystals of 146 mg (quantitative) of the title compound were obtained from 157 mg (0.60 mmol) of 5-(3,4,5-trimethoxyphenyl)penta-(2E,4E)-dienoic acid and 25 mg (0.25 mmol) of homopiperazine. The thus-obtained crude crystals were recrystallized from ethanol, thereby obtaining pale yellow needles.

Melting point: 147–149° C.

$^1$H-NMR (DMSO-$d_6$, 120° C.) δ:

1.81(tt,J=6.0,6.0 Hz,2H), 3.58(dd,J=6.0,6.0 Hz,4H),
3.69(s,4H), 3.72(s,6H), 3.81(s,12H),
6.60(d,J=14.7 Hz,2H), 6.80(s,4H), 6.81(d,J=15.4 Hz,2H),
6.97(dd,J=15.4,10.5 Hz,2H), 7.21(dd,J=14.7,10.5 Hz,2H).

Example 18

Preparation of 1,4-bis[5-(3,5-dimethoxy-4-isopropoxyphenyl)penta-(2E,4E)-dienoyl]hexahydro-1,4-diazepine:

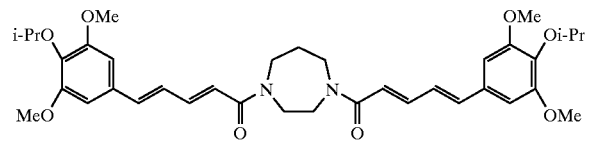

In accordance with the same process as in Example 1, 222 mg (yield: 93%) of the title compound was obtained as a colorless amorphous powder from 220 mg (0.37 mmol) of 5-(3,5-dimethoxy-4-isopropoxyphenyl)penta-(2E,4E)-dienoic acid and 37 mg (0.37 mmol) of homopiperazine.

$^1$H-NMR (DMSO-$d_6$, 120° C.) δ:
1.20(d,J=6.2 Hz,12H), 1.81(tt,J=5.9,5.9 Hz,2H),
3.58(dd,J=5.9,5.9 Hz,4H), 3.69(s,4H), 3.79(s,12H),
4.33(qq,J=6.2,6.2 Hz,2H), 6.59(d,J=14.7 Hz,2H),
6.80(s,4H), 6.82(d,J=15.5 Hz,2H),
6.97(dd,J=15.5,10.6 Hz,2H), 7.22(dd,J=14.7,10.6 Hz,2H).

Example 19

Preparation of 1,4-bis[5-(2-pyridyl)penta-(2E,4E)-dienoyl]hexahydro-1,4-diazepine:

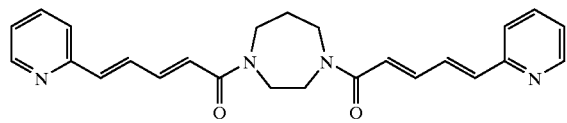

In accordance with the same process as in Example 1, crude crystals were obtained from 230 mg (1.1 mmol) of 5-(2-pyridyl)penta-(2E,4E)-dienoic acid and 49 mg (0.49 mmol) of homopiperazine. The crude crystals were recrystallized from chloroform-ether, thereby obtaining 193 mg (yield: 95%) of the title compound as a colorless crystalline powder.

Melting point: 196–197° C.
$^1$H-NMR (DMSO-$d_6$, 120° C.) δ:
1.81(tt,J=6.0,6.0 Hz,2H), 3.59(dd,J=6.0,6.0 Hz,4H),
3.70(s,4H), 6.74(d,J=14.6 Hz,2H), 6.93(d,J=15.1 Hz,2H),
7.21(ddd,J=7.6,4.8,1.0 Hz,2H),
7.25(dd,J=14.6,11.3 Hz,2H), 7.42(dd,J=15.1,11.3 Hz,2H),
7.42(br d,J=7.6 Hz,2H), 7.71(ddd,J=7.6,7.6,1.8 Hz,2H),
8.52(br d,J=4.8 Hz,2H).

Example 20

Preparation of 1,4-bis[5-(3-pyridyl)penta-(2E,4E)-dienoyl]hexahydro-1,4-diazepine:

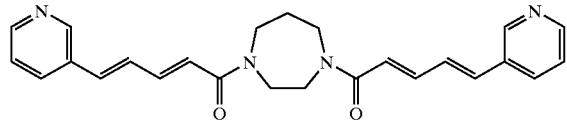

In accordance with the same process as in Example 1, crude crystals of 207 mg (yield: 97%) of the title compound were obtained from 240 mg (1.1 mmol) of 5-(3-pyridyl)penta-(2E,4E)-dienoic acid and 52 mg (0.52 mmol) of homopiperazine. The thus-obtained crude crystals were recrystallized from ethanol-ether, thereby obtaining a colorless crystalline powder.

Melting point: 221–222° C.
$^1$H-NMR (DMSO-$d_6$, 120° C.) δ:
1.81(tt,J=6.0,6.0 Hz,2H), 3.59(dd,J=6.0,6.0 Hz,4H),
3.70(s,4H), 6.67(d,J=13.9 Hz,2H), 6.92(d,J=15.1 Hz,2H),
7.12(dd,J=15.1,10.6 Hz,2H), 7.23(dd,J=13.9,10.6 Hz,2H),
7.32(dd,J=7.9,4.8 Hz,2H), 7.85(ddd,J=7.9,2.2,1.6 Hz,2H),
8.44(dd,J=4.8,1.6 Hz,2H), 8.66(d,J=2.2 Hz,2H).

Example 21

Preparation of 1,4-bis[5-(2-methylthiopyridin-3-yl)penta-(2E,4E)-dienoyl]hexahydro-1,4-diazepine:

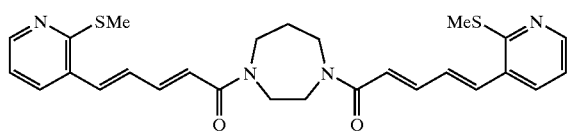

In accordance with the same process as in Example 1, crude crystals of 214 mg (yield: 98%) of the title compound were obtained from 191 mg (0.87 mmol) of 5-(2-methylthio-pyridin-3-yl)penta-(2E,4E)-dienoic acid and 43 mg (0.43 mmol) of homopiperazine. The thus-obtained crude crystals were recrystallized from ethanol-ether, thereby obtaining a colorless crystalline powder.

Melting point: 182–184° C.
$^1$H-NMR (DMSO-$d_6$, 120° C.) δ:
1.80(tt,J=6.0,6.0 Hz,2H), 2.53(s,6H),
3.59(dd,J=6.0,6.0 Hz,4H), 3.69(s,4H),
6.67(d,J=14.7 Hz,2H), 6.93–7.13(m,4H),
7.08(dd,J=7.8,4.6 Hz,2H),
7.23(ddd,J=14.7,8.5,1.6 Hz,2H),
7.78(dd,J=7.8,1.7 Hz,2H), 8.36(dd,J=4.6,1.7 Hz,2H).

Example 22

Preparation of 1,4-bis[5-(2,6-dimethoxypyridin-3-yl) penta-(2E,4E)-dienoyl]hexahydro-1,4-diazepine:

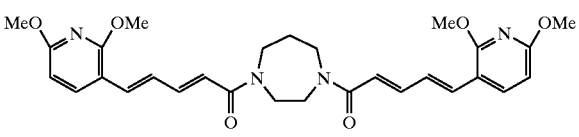

In accordance with the same process as in Example 1, crude crystals of 220 mg (yield: 99%) of the title compound were obtained from 194 mg (0.83 mmol) of 5-(2,6-dimethoxy-pyridin-3-yl)penta-(2E,4E)-dienoic acid and 42 mg (0.42 mmol) of homopiperazine. The thus-obtained crude crystals were recrystallized from chloroform-ether, thereby obtaining a pale yellow crystalline powder.

Melting point: 227–230° C.
$^1$H-NMR (DMSO-$d_6$, 120° C.) δ:
1.79(tt,J=6.0,6.0 Hz,2H), 3.56(dd,J=6.0,6.0 Hz,4H),
3.67(s,4H), 3.89(s,6H), 3.96(s,6H),
6.35(d,J=8.1 Hz,2H), 6.51(d,J=14.5 Hz,2H),
6.87(br d,J=15.5 Hz,2H), 6.96(dd,J=15.5,9.4 Hz,2H),
7.19(ddd,J=14.5,9.4,0.9 Hz,2H), 7.76(d,J=8.1 Hz,2H).

Example 23

Preparation of 1,4-bis[5-(3-quinolyl)penta-(2E,4E)-dienoyl]hexahydro-1,4-diazepine:

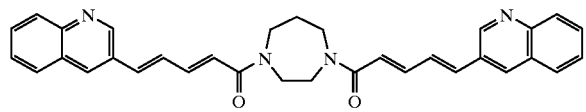

In accordance with the same process as in Example 1 crude crystals were obtained from 180 mg (0.84 mmol) of 5-(3-quinolyl)penta-(2E,4E)-dienoic acid and 38 mg (0.38 mmol) of homopiperazine. The crude crystals were recrystallized from methanol, thereby obtaining 124 mg (yield: 63%) of the title compound as colorless needles.

Melting point: 222–223° C.

$^1$H-NMR (DMSO-$d_6$, 120° C.) (mixture of amide rotamers) δ:
1.84(tt,J=6.0,6.0 Hz,2H), 3.62(dd,J=6.0,6.0 Hz,4H),
3.73(s,4H), 6.67–6.79(m,2H), 7.04–7.16(m,2H),
7.24–7.37(m,4H), 7.55(ddd,J=8.3,7.0,1.1 Hz,2H),
7.69(ddd,J=8.3,7.0,1.5 Hz,2H), 7.87(br d,J=8.3 Hz,2H),
7.96(br d,J=8.3 Hz,2H), 8.31(br d,J=2.0 Hz,2H),
9.04(d,J=2.0 Hz,2H).

Example 24

Preparation of 1,4-bis[5-(4-quinolyl)penta-(2E,4E)-dienoyl]hexahydro-1,4-diazepine:

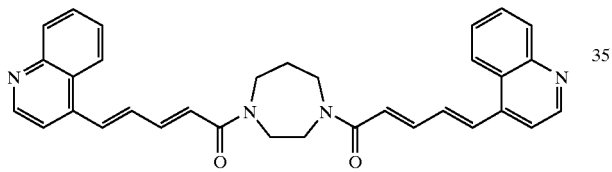

In accordance with the same process as in Example 1, 124 mg (yield: 34%) of the title compound was obtained as a pale brown amorphous powder from 347 mg (1.5 mmol) of 5-(4-quinolyl)penta-(2E,4E)-dienoic acid and 70 mg (0.70 mmol) of homopiperazine.

$^1$H-NMR (CDCl$_3$) (mixture of amide rotamers) δ:
1.75–2.15(m,2H), 3.60–3.90(m,8H),
6.58(d,J=14.7 Hz,1.3H), 6.62(d,J=14.7 Hz,0.7H),
7.07–7.22(m,2H), 7.47–7.78(m,10H), 8.00–8.20(m,4H),
8.90(d,J=4.4 Hz,1.3H), 8.90(d,J=4.4 Hz,0.7H).

Example 25

Preparation of 1,4-bis[5-(8-quinolyl)penta-(2E,4E)-dienoyl]hexahydro-1,4-diazepine:

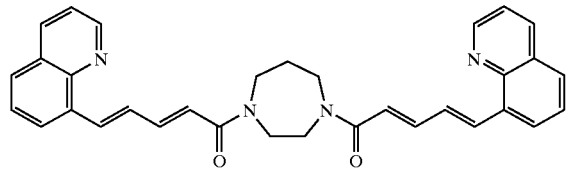

In accordance with the same process as in Example 1, 248 mg (yield: 69%) of the title compound was obtained as a pale yellow amorphous powder from 330 mg (1.5 mmol) of 5-(8-quinolyl)penta-(2E,4E)-dienoic acid and 70 mg (0.70 mmol) of homopiperazine.

$^1$H-NMR (CDCl$_3$) (mixture of amide rotamers) δ:
1.97–2.12(m,2H), 3.58–3.88(m,8H),
6.50(br d,J=14.7 Hz,1.5H), 6.53(br d,J=14.7 Hz,0.5H),
7.22–7.40(m,2H), 7.44(br dd,J=8.1,4.2 Hz,2H),
7.55(br dd,J=7.8,7.8 Hz,2H), 7.61–7.85(m,2H),
7.78(br d,J=7.8 Hz,2H), 7.97(br d,J=7.8 Hz,2H),
8.08–8.26(m,2H), 8.16(br d,J=8.1 Hz,2H), 8.97(br s,2H).

Example 26

Preparation of 1,4-bis[5-(3-methoxyphenyl)penta-(2E,4E)-dienoyl]piperazine:

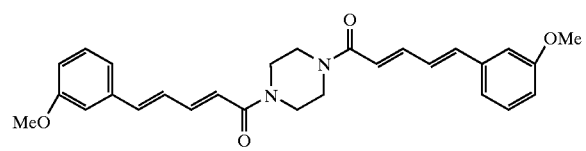

In accordance with the same process as in Example 1, crude crystals of 304 mg (yield: 94%) of the title compound were obtained from 300 mg (1.5 mmol) of 5-(3-methoxyphenyl)penta-(2E,4E)-dienoic acid and 60 mg (0.70 mmol) of piperazine. The thus-obtained crude crystals were recrystallized from chloroform-ether, thereby obtaining colorless needles.

Melting point: 175–177° C.

$^1$H-NMR (DMSO-$d_6$, 120° C.) δ:
3.62(s,8H), 3.79(s,6H), 6.68(d,J=14.6 Hz,2H),
6.86(ddd,J=1.2,2.2,8.1 Hz,2H), 6.90(d,J=15.5 Hz,2H),
7.03(dd,J=10.3,15.5 Hz,2H), 7.03–7.11(m,4H),
7.25(dd,J=10.3,14.6 Hz,2H), 7.26(dd,J=8.1,8.1 HZ,2H).

Example 27

Preparation of 1,4-bis[5-(2,6-dimethoxyphenyl)penta-(2E,4E)-dienoyl]piperazine:

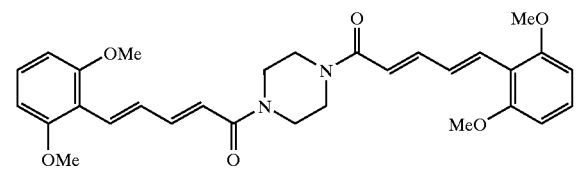

In accordance with the same process as in Example 1, crude crystals were obtained from 172 mg (0.87 mmol) of 5-(2,6-dimethoxyphenyl)penta-(2E,4E)-dienoic acid and 31 mg (0.37 mmol) of piperazine. The crude crystals were recrystallized from chloroform-ether-hexane, thereby obtaining 145 mg (yield: 77%) of the title compound as a colorless crystalline powder.

Melting point: at least 270° C.

$^1$H-NMR (DMSO-$d_6$, 120° C.) 67 :
3.61(s,8H), 3.84(s,12H), 6.55(d,J=14.2 Hz,2H),
6.67(d,J=8.4 Hz,4H), 7.10(d,J=15.4 Hz,2H),
7.21(t,J=8.4 Hz,2H), 7.22(dd,J=14.2,10.7 Hz,2H),
7.31(dd,J=15.4,10.7 Hz,2H).

Example 28

Preparation of 1,4-bis[5-(4-tert-butyl-2-methoxyphenyl)penta-(2E,4E)-dienoyl]piperazine:

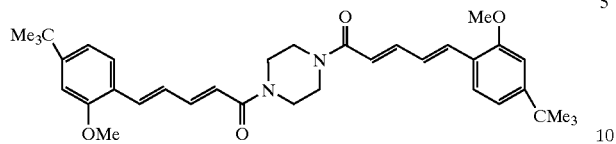

In accordance with the same process as in Example 1, crude crystals were obtained from 234 mg (0.90 mmol) of 5-(4-tert-butyl-2-methoxyphenyl)penta-(2E,4E)-dienoic acid and 39 mg (0.45 mmol) of piperazine. The crude crystals were recrystallized from ethanol-ether, thereby obtaining 171 mg (yield: 66%) of the title compound as a colorless crystalline powder.

Melting point: 200–204° C.
$^1$H-NMR (DMSO-$d_6$, 120° C.) δ:
1.30(s,18H), 3.61(s,8H), 3.86(s,6H),
6.60(d,J=14.5 Hz,2H), 6.95–7.07(m,8H),
7.25(ddd,J=14.5,9.2,1.0 Hz,2H), 7.42(d,J=9.2 Hz,2H).

Example 29

Preparation of 1,4-bis[5-(3,4,5-trimethoxyphenyl)-penta-(2E,4E)-dienoyl]piperazine:

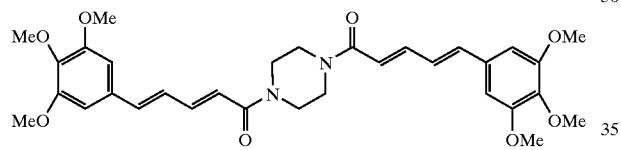

In accordance with the same process as in Example 1, crude crystals of 141 mg (yield: 80%) of the title compound were obtained from 161 mg (0.61 mmol) of 5-(3,4,5-trimethoxyphenyl)penta-(2E,4E)-dienoic acid and 37 mg (0.43 mmol) of piperazine. The thus-obtained crude crystals were recrystallized from methanol-ether-chloroform, thereby obtaining pale yellow needles.

Melting point: 207–210° C.
$^1$H-NMR (CDCl$_3$) (mixture of amide rotamers) δ:
3.55–3.85(m,8H), 3.87(s,6H), 3.90(s,12H),
6.46(d,J=14.4 Hz,2H), 6.69(s,4H), 6.75–6.95(m,4H),
7.49(br dd,J=14.4,6.2 Hz,1H),
7.51(br dd,J=14.4,6.2 Hz,1H).

Example 30

Preparation of 1,4-bis[5-(3,5-dimethoxy-4-isopropoxyphenyl)penta-(2E,4E)-dienoyl]piperazine:

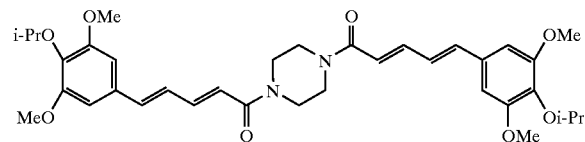

In accordance with the same process as in Example 1, crude crystals were obtained from 193 mg (0.66 mmol) of 5-(3,5-dimethoxy-4-isopropoxyphenyl)penta-(2E,4E)-dienoic acid and 29 mg (0.33 mmol) of piperazine. The crude crystals were recrystallized from ethanol-ether-hexane, thereby obtaining 167 mg (yield: 81%) of the title compound as colorless flakes.

Melting point: 196–199° C.
$^1$H-NMR (DMSO-$d_6$, 120° C.) δ:
1.20(d,J=6.1 Hz,12H), 3.62(s,8H), 3.80(s,12H),
4.33(qq,J=6.1,6.1 Hz,2H), 6.64(d,J=14.7 Hz,2H),
6.81(s,4H), 6.84(d,J=15.4 Hz,2H),
6.97(dd,J=15.4,10.3 Hz,2H), 7.25(dd,J=14.7,10.3 Hz,2H).

Example 31

Preparation of 1,4-bis[5-(4-quinolyl)penta-(2E,4E)-dienoyl]piperazine:

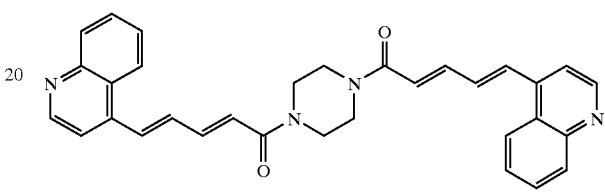

In accordance with the same process as in Example 1, 171 mg (yield: 48%) of the title compound were obtained as colorless amorphous powder from 331 mg (1.5 mmol) of 5-(4-quinolyl)penta-(2E,4E)-dienoic acid and 60 mg (0.70 mmol) of piperazine.

$^1$H-NMR (CDCl$_3$) δ:
3.60–3.92(m,8H), 6.60(d,J=14.6 Hz,2H),
7.15(dd,J=15.4,10.7 Hz,2H), 7.54(d,J=4.6 Hz,2H),
7.58–7.69(m,4H), 7.65(br dd,J=7.1,7.1 Hz,2H),
7.76(ddd,J=8.5,7.1,1.5 Hz,2H), 8.13(dd,J=7.1,1.5 Hz,2H),
8.14(dd,J=8.5,1.5 Hz,2H), 8.91(d,J=4.6 Hz,2H).

Example 32

Preparation of 1,4-bis[5-(8-quinolyl)penta-(2E,4E)-dienoyl]piperazine:

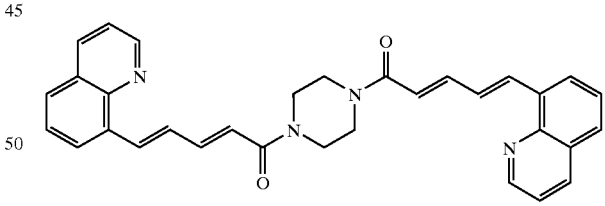

In accordance with the same process as in Example 1, 168 mg (yield: 56%) of the title compound was obtained as a pale yellow amorphous powder from 284 mg (1.3 mmol) of 5-(8-quinolyl)penta-(2E,4E)-dienoic acid and 53 mg (0.60 mmol) of piperazine.

$^1$H-NMR (DMSO-$d_6$, 120° C.) (mixture of amide rotamers) δ:
3.68(m,8H), 6.67–6.84(m,2H), 7.34–7.52(m,4H),
7.53(dd,J=8.3,4.2 Hz,2H), 7.60(dd,J=8.1,7.5 Hz,2H),
7.90(d,J=8.1 Hz,2H), 7.93–8.16(m,2H),
8.04(d,J=7.5 Hz,2H), 8.32(dd,J=8.3,1.9 Hz,2H),
8.95(dd,J=4.2,1.9 Hz,2H).

Example 33

Preparation of ethyl 1,4-bis[5-(3,4,5-trimethoxy-phenyl)penta-(2E,4E)-dienoyl]piperazine-2-carboxylate:

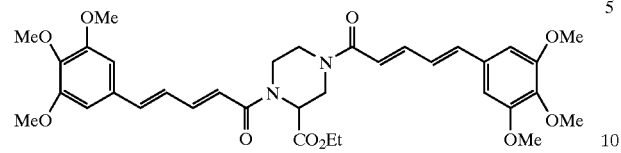

A suspension of 231 mg (1.0 mmol) of ethyl piperazine-2-carboxylate dihydrochloride[(1)] in anhydrous dimethylformamide (4 ml) was cooled in an ice bath. To the suspension were added 0.84 ml (6.0 mmol) of triethylamine, 582 mg (2.2 mmol) of 5-(3,4,5-trimethoxyphenyl)penta-(2E,4E)-dienoic acid, and 0.33 ml (2.2 mmol) of diethyl phosphorocyanidate. The ice bath was removed, and the mixture was stirred for 1 hour at room temperature. Added to the reaction mixture were 4 ml of a 5% aqueous solution of sodium hydrogencarbonate to conduct extraction with chloroform. An organic layer was dried over anhydrous sodium sulfate, and then concentrated under reduced pressure. The resultant crude oil (600 mg) was purified by column chromatography on alumina and column chromatography on silica gel to obtain 511 mg (yield: 79%) of the title compound as a pale yellow amorphous powder.

(1) Jucker, von E.; Rissi, E., Helvetica Chim. Acta, 1962, 2383–2402.

$^1$H-NMR (DMSO-$d_6$, 120° C.) δ:
1.19(t,J=7.3 Hz,3H), 3.05–3.19(m,1H), 3.25–3.48(m,2H), 3.73(s,6H), 3.82(s,12H), 4.04–4.21(m,2H),
4.12(q,J=7.3 Hz,2H), 4.54–4.63(m,1H), 5.03–5.08(m,1H),
6.61(d,J=14.7 Hz,1H), 6.64(d,J=14.7 Hz,1H), 6.82(s,4H), 6.85(d,J=15.6 Hz,1H), 6.87(d,J=15.6 Hz,1H),
6.98(dd,J=15.6,10.0 Hz,2H), 7.24(dd,J=14.7,10.0 Hz,1H),
7.27(dd,J=14.7,10.0 Hz,1H).

Example 34

Preparation of 1,4-bis[5-(3,4,5-trimethoxyphenyl)-penta-(2E,4E)-dienoyl]piperazine-2-carboxylic acid:

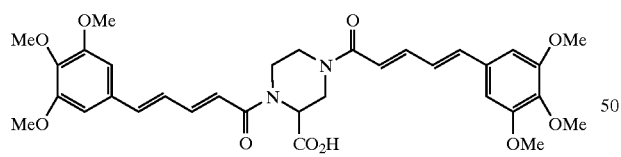

Added to a solution of 339 mg (0.52 mmol) of ethyl 1,4-bis[5-(3,4,57trimethoxyphenyl)penta-(2E,4E)-dienoyl]piperazine-2-carboxylate synthesized by the process of Example 33 in methanol-tetrahydrofuran (1 ml–1.5 ml) was 0.50 ml (1.5 mmol) of a 3N aqueous solution of potassium hydroxide, and the mixture was stirred for 1 hour at room temperature. A saturated saline solution (3 ml) and 1N hydrochloric acid (2 ml) were added to the reaction mixture to conduct extraction with chloroform. An organic layer was dried over anhydrous sodium sulfate, and then concentrated under reduced pressure. The resultant crude oil (356 mg) was purified by column chromatography on silica gel to obtain 325 mg (quantitative) of the title compound as a pale yellow amorphous powder.

The amorphous powder was recrystallized from ethyl acetate-ethyl ether to obtain a pale yellow crystalline powder.

Melting point: 212° C. (decomposed).

$^1$H-NMR (DMSO-$d_6$, 120° C.) (no OH proton of the carboxyl group was observed) δ:
2.98–3.12(m,1H), 3.25–3.42(m,2H), 3.72(s,6H), 3.82(s,12H), 4.02–4.23(m,2H), 4.56–4.65(m,1H), 4.80–4.90(m,1H), 6.62(d,J=14.7 Hz,1H),
6.65(d,J=14.7 Hz,1H), 6.82(s,2H), 6.83(s,2H), 6.83(d,J=15.4 Hz,1H), 6.84(d,J=15.4 Hz,1H),
6.97(dd,J=15.4,10.4 Hz,1H), 6.98(dd,J=15.4,10.4 Hz,1H),
7.22(dd,J=14.7,10.4 Hz,1H), 7.24(dd,J=14.7,10.4 Hz,1H).

Example 35

Preparation of 1,4-bis[5-(3,4,5-trimethoxyphenyl)-penta-(2E,4E)-dienoyl]-N-methylpiperazine-2-carbohydroxamic acid:

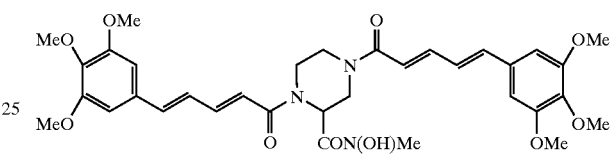

Added to a solution of 148 mg (0.24 mmol) of 1,4-bis[5-(3,4,5-trimethoxyphenyl)penta-(2E,4E)-dienoyl]-piperazine-2-carboxylic acid synthesized by the process of Example 34 in anhydrous dimethylformamide (0.5 ml) was 44.9 mg (0.28 mmol) of 1,1'-carbonyldiimidazole. After the mixture was stirred for 15 minutes, 24.9 mg (0.30 mmol) of N-methylhydroxyamine hydrochloride and 0.050 ml (0.36 mmol) of triethylamine were added, and the mixture was stirred for an additional 15 minutes. Added to the reaction mixture was 3 ml of 0.5N hydrochloric acid to conduct extraction with chloroform. An organic layer was dried over anhydrous sodium sulfate, and then concentrated under reduced pressure. The resultant crude oil (179 mg) was purified by column chromatography on silica gel to obtain 134.6 mg (yield: 87%) of the title compound as pale yellow amorphous powder.

$^1$H-NMR (CDCl$_3$) (mixture of amide rotamers; no OH proton was observed) δ:
2.85(br s,3H), 3.15–4.05(m,4H), 3.87(s,9H), 3.91(s,9H), 4.40–4.85(m,2H), 5.35–5.60(m,1H),
6.35–6.60(m,2H), 6.69(s,4H), 6.65–6.95(m,4H),
7.40–7.60(m,2H).

Referential Example 2

Preparation of 2-(N,N-dimethylaminomethyl)piperazine trihydrochloride [(2)]:

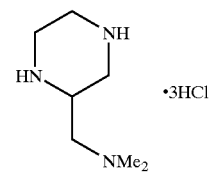

A solution of 5.2 g (17 mmol) of 1,4-benzyl-2-hydroxymethyl)piperazine[(1)] in anhydrous methylene chloride (45 ml) was cooled in an ice bath. To the solution was added 1.6 ml (21 mmol) of methanesulfonyl chloride with stirring. The ice bath was removed, and the mixture was stirred for 13 hours at room temperature. Added to the reaction mixture were 40 ml of a 5% aqueous solution of sodium hydrogencarbonate to conduct extraction with methylene chloride. An organic layer was dried over anhydrous sodium sulfate, and then concentrated under reduced pressure. The resultant crude oil (4.7 g) was dissolved in anhydrous dimethylformamide (15 ml). To the solution were added 3.0 g (38 mmol) of dimethylamine hydrochloride, 5.2 g (38 mmol) of potassium carbonate, and 6.2 g (38 mmol) of potassium iodide, and the resultant mixture was stirred for 5 hours at 50° C. Water was added to the reaction mixture to conduct extraction with chloroform. An organic layer was dried over anhydrous sodium sulfate, and then concentrated under reduced pressure. The resultant crude oil was purified by column chromatography on alumina and column chromatography on silica gel to obtain 3.2 g (yield: 67%) of 1,4-dibenzyl-2-(N,N-dimethyl-aminomethyl)piperazine as a colorless oil.

Added to a solution of 3.1 g (10 mmol) of 1,4-benzyl-2-(N,N-dimethylaminomethyl)piperazine synthesized by the above process in methanol (25 ml) were 5 ml (60 mmol) of concentrated hydrochloric acid and 0.50 g of 10% palladium on carbon. The resultant mixture was stirred for 14 hours at 55° C. under hydrogen. To the reaction mixture was added 12 ml of water, and the catalyst was removed by suction filtration through Celite. The filtrate was concentrated under reduced pressure, thereby obtaining 2.4 g (yield: 99%) of the title compound as a colorless crystalline powder.

Melting point: 265° C. (decomposed).

(1) Jucker, von E.; Rissi, E., Helvetica Chim. Acta, 1962, 2383–2402.

(2) Miyamoto, T.; Matsumoto, J.; Chiba, K.; Egawa, H.; Shibamori, K.; Minamide, A.; Nishimura, Y.; Okada, H.; Kataoka, M.; Fujita, M.; Hirose, T.; Nakano, J., J. Med. Chem., 1990, 33, 1465–1656.

Example 36

Preparation of 1,4-bis[5-(3,4,5-trimethoxyphenyl)-penta-(2E,4E)-dienoyl]-2-(N,N-dimethylaminomethyl)-piperazine hydrochloride:

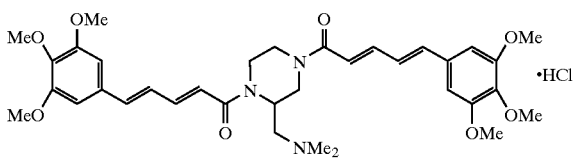

In accordance with the same process as in Example 33, 371 mg (yield: 58%) of 1,4-bis[5-(3,4,5-trimethoxyphenyl)-penta-(2E,4E)-dienoyl]-2-(N,N-dimethylaminomethyl)-piperazine was obtained as a pale yellow amorphous powder from 528 mg (2.0 mmol) of 5-(3,4,5-trimethoxyphenyl) penta-(2E,4E)-dienoic acid and 252 mg (1.0 mmol) of 2-(N,N-dimethylaminomethyl)piperazine trihydrochloride synthesized by the process described in Referential Example 2. Added to a solution of 110 mg (0.17 mmol) of the thus-obtained amorphous powder in ethanol (10 ml) was 0.35 ml (0.35 mmol) of 1N hydrochloric acid, and the resultant mixture was concentrated under reduced pressure, thereby obtaining the title compound as a pale yellow amorphous powder.

$^1$H-NMR (DMSO-$d_6$, 120° C.) (no N$^+$H proton of the ammonium salt was observed) δ:

2.81(br s,6H), 2.87–3.50(m,5H), 3.72(s,6H), 3.82(s,12H), 3.99–4.38(m,3H), 5.01(m,1H), 6.74(br d,J=14.7 Hz,2H), 6.83(s,2H), 6.84(s,2H), 6.89(br d,J=15.5 Hz,2H), 7.03(dd,J=15.5,10.5 Hz,1H), 7.04(dd,J=15.5,10.5 Hz,1H), 7.29(dd,J=14.7,10.5 Hz,1H), 7.30(dd,J=14.7,10.5 Hz,1H).

Example 37

Preparation of 1,4-bis[5-(3,4,5-trimethoxyphenyl)-penta-(2E,4E)-dienoyl]-2-(N,N-diisopropylaminomethyl)-piperazine fumarate:

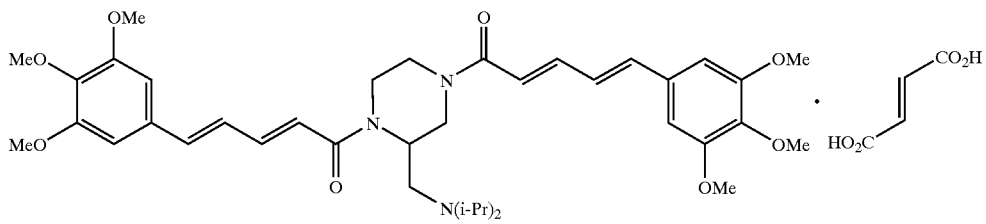

In accordance with the same process as in Example 33, 108 mg (yield: 57%) of 1,4-bis[5-(3,4,5-trimethoxyphenyl)-penta-(2E,4E)-dienoyl]-2-(N,N-diisopropylaminomethyl)-piperazine was obtained as a pale yellow amorphous powder from 153 mg (0.58 mmol) of 5-(3,4,5-trimethoxyphenyl) penta-(2E,4E)-dienoic acid and 85 mg (0.27 mmol) of 2-(N,N-di-isopropylaminomethyl)piperazine trihydrochloride synthesized by the same process as in Referential Example 2. Added to a solution of 88 mg (0.12 mmol) of the thus-obtained amorphous powder in ethanol (10 ml) was 15 mg (0.12 mmol) of fumaric acid, and the resultant mixture was concentrated under reduced pressure, thereby obtaining the title compound as a pale yellow amorphous powder.

$^1$H-NMR (data for free base of the title compound) (DMSO-$d_6$, 120° C.) δ:

0.95(d,J=6.6 Hz,6H), 0.98(d,J=6.6 Hz,6H), 2.51–2.56(m,2H), 3.03(qq,J=6.6,6.6 Hz,2H), 2.95–3.30(m,3H), 3.72(s,6H), 3.82(s,12H), 4.02–4.45(m,4H), 6.65(br d,J=14.7 Hz,2H), 6.81(s,2H), 6.82(s,2H), 6.84(d,J=15.5 Hz,1H), 6.85(d,J=15.5 Hz,1H), 6.96(dd,J=15.5,10.4 Hz,1H), 7.00(dd,J=15.5,10.4 Hz,1H), 7.24(dd,J=14.7,10.4 Hz,1H), 7.26(dd,J=14.7,10.4 Hz,1H).

Example 38

Preparation of 1,4-bis[5-(3,4,5-trimethoxyphenyl)-penta-(2E,4E)-dienoyl]-2-morpholinomethylpiperazine fumarate:

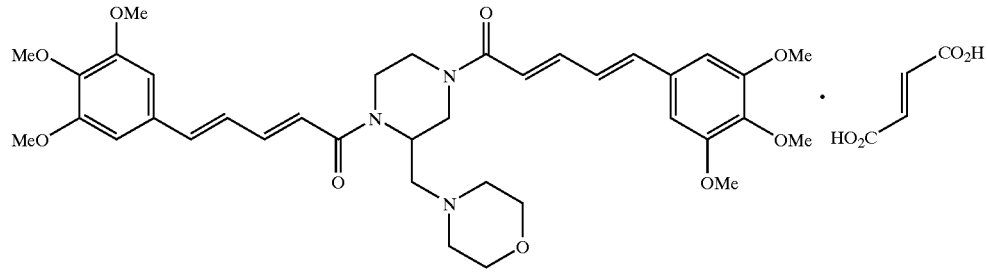

In accordance with the same process as in Example 33, 234 mg (yield: 62%) of 1,4-bis[5-(3,4,5-trimethoxyphenyl)-penta-(2E,4E)-dienoyl]-2-morpholinomethylpiperazine was obtained as pale yellow amorphous powder from 325 mg (1.2 mmol) of 5-(3,4,5-trimethoxyphenyl)penta-(2E,4E)-dienoic acid and 165 mg (0.55 mmol) of 2-morpholinomethyl-piperazine trihydrochloride synthesized by the same process as in Referential Example 2. Added to a solution of 204 mg (0.30 mmol) of the thus-obtained amorphous powder in ethanol (10 ml) was 35 mg (0.30 mmol) of fumaric acid, and the resultant mixture was concentrated under reduced pressure, thereby obtaining the title compound as a pale yellow amorphous powder.

$^1$H-NMR (DMSO-$d_6$, 120° C.) (neither N$^+$H proton of the ammonium salt nor OH proton of the carboxyl group was observed) δ:

2.30–2.50(m,6H), 2.95–3.25(m,3H), 3.56–3.66(m,4H),
3.79(s,6H), 3.88(s,12H), 4.08–4.65(m,4H),
6.68(br d,J=14.4 Hz,2H), 6.69(s,2H), 6.87(s,4H),
6.90(d,J=15.5 Hz,1H), 6.90(d,J=15.5 Hz,1H),
7.02(dd,J=15.5,10.2 Hz,2H), 7.30(dd,J=14.4,10.2 Hz,1H),
7.32(dd,J=14.4,10.2 Hz,1H).

Example 39

Preparation of 1,4-bis[5-(3,4,5-trimethoxyphenyl)-penta-(2E,4E)-dienoyl]-2-(imidazol-1-ylmethyl)piperazine fumarate:

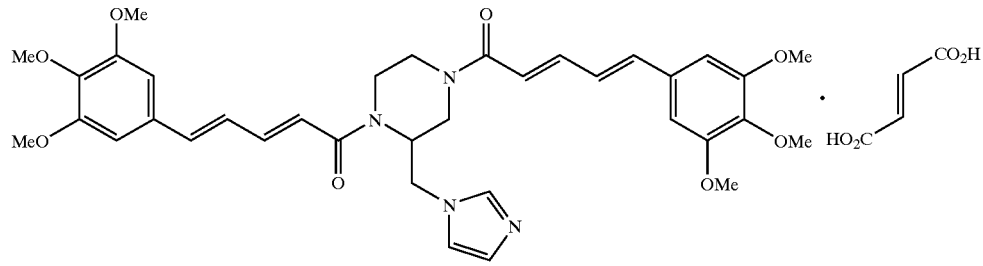

In accordance with the same process as in Example 33, 74 mg (yield: 30%) of 1,4-bis[5-(3,4,5-trimethoxyphenyl)-penta-(2E,4E)-dienoyl]-2-(imidazol-1-ylmethyl)piperazine was obtained as a pale yellow amorphous powder from 221 mg (0.83 mmol) of 5-(3,4,5-trimethoxyphenyl)penta-(2E,4E)-dienoic acid and 105 mg (0.38 mmol) of 2-(imidazol-1-ylmethyl)piperazine trihydrochloride synthesized by the same process as in Referential Example 2. Added to a solution of 74 mg (0.11 mmol) of the thus-obtained amorphous powder in ethanol (10 ml) was 13 mg (0.11 mmol) of fumaric acid, and the resultant mixture was concentrated under reduced pressure, thereby obtaining the title compound as a pale yellow amorphous powder.

$^1$H-NMR (DMSO-$d_6$, 120° C.) (neither N$^+$H proton of the ammonium salt nor OH proton of the carboxyl group was observed) δ:

3.02–3.57(m,5H), 3.74(s,6H), 3.82(s,12H),
4.05–4.28(m,3H), 4.64–4.78(m,1H), 6.33–6.48(m,2H),
6.60–6.94(m,5H), 6.62(s,2H), 6.80(s,2H), 6.82(s,2H),
7.08(t,J=1.0 Hz,1H), 7.11–7.33(m,2H), 7.47–7.53(m,1H).

Example 40

Preparation of 1,4-bis[5-(3,4,5-trimethoxyphenyl)-penta-(2E,4E)-dienoyl]-2-phenylthiomethylpiperazine:

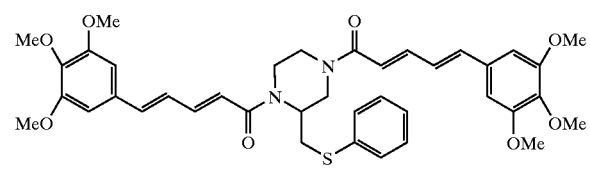

In accordance with the same process as in Example 33, 270 mg (yield: 56%) of the title compound was obtained as a pale yellow amorphous powder from 489 mg (1.7 mmol) of 5-(3,4,5-trimethoxyphenyl)penta-(2E,4E)-dienoic acid and 203 mg (0.69 mmol) of 2-phenylthiomethylpiperazine dihydrochloride synthesized by the same process as in Referential Example 2.

$^1$H-NMR (CDCl$_3$) δ:

2.97–3.33(m,3H), 3.16(d,J=7.6 Hz,2H), 3.73(s,3H),
3.73(s,3H), 3.83(s,6H), 3.84(s,6H), 4.07–4.21(m,2H), 4.29–4.44(m,1H), 4.44–4.58(m,1H), 6.43(d,J=14.7 Hz,1H),
6.63(d,J=14.7 Hz,1H), 6.74–6.92(m,3H), 6.80(s,2H), 6.82(s,2H), 6.97(dd,J=15.5,10.1 Hz,1H),
7.16–7.35(m,5H), 7.39–7.46(m,2H).

Example 41

Preparation of 1,4-bis[5-(3,4,5-trimethoxyphenyl)-penta-(2E,4E)-dienoyl]-1,2,3,4-tetrahydroquinoxaline:

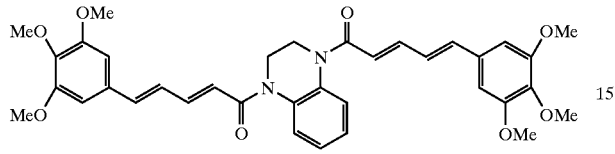

A solution of 185 mg (0.70 mmol) of 5-(3,4,5-trimethoxyphenyl)penta-(2E,4E)-dienoic acid in anhydrous dimethylformamide-methylene chloride (0.2 ml–2 ml) was cooled in an ice bath. To the solution was added 0.10 ml (1.1 mmol) of oxalyl chloride with stirring. The ice bath was removed, and the mixture was stirred for 30 minutes at room temperature. The reaction mixture was concentrated under reduced pressure to obtain crude crystals of 5-(3,4,5-trimethoxyphenyl)penta-(2E,4E)-dienoyl chloride.

A solution of 5-(3,4,5-trimethoxyphenyl)penta-(2E,4E)-dienoyl chloride in methylene chloride (3 ml) was added dropwise to a solution of 45 mg (0.34 mmol) of 1,2,3,4-tetrahydroquinoxaline[1] in pyridine (0.5 ml) over about 5 minutes with stirring in an ice bath. After completion of the addition, the mixture was stirred for 1 hour and water was added to conduct extraction with chloroform. An organic layer was dried over anhydrous sodium sulfate and then concentrated under reduced pressure. The resultant crude oil (254 mg) was purified by column chromatography on alumina and column chromatography on silica gel to obtain 91 mg (yield: 43%) of crude crystals of the title compound. The crude crystals were recrystallized from chloroform-ether to obtain pale yellow fien needles.
(1) Bugle, R. C.; Osteryoung, R. A., J. Org. Chem., 1979, 44, 1719–1720.
Melting point: 183–185° C.
$^1$H-NMR (DMSO-$d_6$, 120° C.) δ:
3.71(s,6H), 3.80(s,12H), 3.97(s,4H),
6.52(d,J=14.9 Hz,2H), 6.80(s,4H), 6.85–7.00(m,4H),
7.21–7.28(m,2H), 7.36(ddd,J=14.9,9.0,1.1 Hz,2H),
7.38–7.45(m,2H).

Example 42

Preparation of 1,4-bis[5-(3,4,5-trimethoxyphenyl)-penta-(2E,4E)-dienoyl]-pyrido[2,3-b]-1,2,3,4-tetrahydropyrazine:

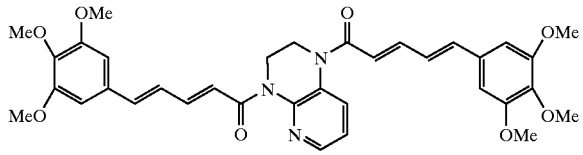

In accordance with the same process as in Example 41, 190 mg (yield: 40%) of crude crystals of the title compound were obtained from 477 mg (1.8 mmol) of 5-(3,4,5-trimethoxyphenyl)penta-(2E,4E)-dienoic acid and 102 mg (0.75 mmol) of pyrido[2,3-b]-1,2,3,4-tetrahydropyrazine[1]. The crude crystals were recrystallized from ethanol to obtain pale yellow fine needles.
(1) Bugle, R. C.; Osteryoung, R. A., J. Org. Chem, 1979, 44, 1719–1720.
Melting point: 183–185° C.
$^1$H-NMR (DMSO-$d_6$, 120° C.) δ:
3.72(s,3H), 3.73(s,3H), 3.81(s,6H), 3.81(s,6H),
4.00(s,4H), 6.58(d,J=14.7 Hz,1H), 6.83(s,2H),
6.83(s,2H), 6.88–7.05(m,5H), 7.21(dd,J=8.1,4.8 Hz,1H),
7.35(ddd,J=14.7,8.9,1.1 Hz,1H),
7.39(ddd,J=14.7,8.9,1.1 Hz,1H),
8.02(dd,J=8.1,1.7 Hz,1H), 8.19(dd,J=4.8,1.7 Hz,1H).

Referential Example 3

Preparation of 6-(N,N-dimethylamino)hexahydro-1,4-diazepine.trihydrobromide:

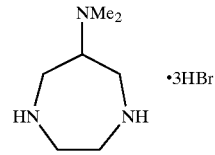

To a solution of 0.53 ml (6.1 mmol) of oxalyl chloride in anhydrous tetrahydrofuran (15 ml) at −78° C. under nitrogen was added dropwise a solution of 0.50 ml (7.0 mmol) of anhydrous dimethyl sulfoxide in anhydrous tetrahydrofuran (2 ml). After 10 minutes, a solution of 2.0 g (4.7 mmol) of 1,4-bis(p-toluenesulfonyl)-6-hydroxy-hexahydro-1,4-diazepine[1] in anhydrous dimethyl sulfoxide-tetrahydrofuran (2 ml–5 ml) was added dropwise. After 20 minutes at −78° C., 1.3 ml (9.3 mmol) of triethylamine was added dropwise. The cooling bath was removed, and the mixture was stirred for 45 minutes at room temperature. Water (3 ml) and a saturated saline solution (3 ml) were added to the reaction mixture to conduct extraction with ether. An organic layer was dried over anhydrous sodium sulfate and then concentrated under reduced pressure, and the resultant crude oil was purified by chromatography on silica gel, thereby obtaining 1.0 g (yield: 52%) of 1,4-bis (p-toluenesulfonyl)-6-oxohexahydro-1,4-diazepine as a colorless oil.

Addition of 102 mg (1.8 mmol) of potassium hydroxide to a solution of 479 mg (5.9 mmol) of dimethylamine hydrochloride in methanol (4 ml) gave a clear solution. To this solution were added 979 mg (2.3 mmol) of 1,4-bis(p-toluenesulfonyl)-6-oxohexahydro-1,4-diazepine synthesized by the above process in methanol (30 ml) and 116 mg (1.8 mmol) of sodium cyanoborohydride. After the resultant mixture was stirred for 15 hours at room temperature, 104 mg (1.7 mmol) of additional sodium cyanoborohydride was added, and the mixture was stirred for an additional 25 hours. A 1N aqueous solution (5 ml) of sodium hydroxide was added to the reaction mixture, and the mixture was concentrated under reduced pressure, followed by extraction with chloroform. An organic layer was dried over anhydrous sodium sulfate and then concentrated under reduced pressure. The resultant crude oil was purified by column chromatography on silica gel to obtain 519 mg (yield: 50%) of 1,4-bis(p-toluenesulfonyl)-6-(N,N-dimethylamino)-hexahydro-1,4-diazepine as a colorless oil.

Weighed out to a reaction vessel was 250 mg (0.56 mmol) of 1,4-bis(p-toluenesulfonyl)-6-(N,N-dimethylamino)- hexahydro-1,4-diazepine synthesized by the above process, and 0.20 ml (2.3 mmol) of phenol and a 30% acetic acid solution (4 ml) of hydrobromic acid were added, followed by stirring for 6 hours in a bath controlled to 70° C. After the reaction mixture was concentrated under reduced pressure, diethyl ether (5 ml) was added to the residue with stirring, and a supernatant was removed. This process was repeated twice to remove diethyl ether-soluble material. The residue was concentrated again under reduced pressure to completely remove diethyl ether. Ethanol (2 ml) was added to the resultant residue, and the mixture was stirred for 30 minutes. Diethyl ether (2 ml) was added to the resultant solution, and the mixture was cooled in an ice bath, thereby obtaining 194 mg (yield: 91%) of the title compound as a colorless crystalline powder (melting point: 245° C., decomposed).

(1) Saari. W. S.; Raab, A. W.; King, S. W., J. Org. Chem., 1971, 36, 1711–1714.

Example 43

Preparation of 1,4-bis[5-(3,4,5-trimethoxyphenyl)-penta-(2E,4E)-dienoyl]-6-(N,N-dimethylamino)hexahydro-1,4-diazepine hydrochloride:

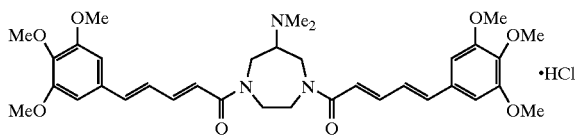

In accordance with the same process as in Example 33, 255 mg (quantitative) of 1,4-bis[5-(3,4,5-trimethoxyphenyl)penta-(2E,4E)-dienoyl]-6-(N,N-dimethylamino)-hexahydro-1,4-diazepine were obtained as a colorless amorphous powder from 254 mg (0.96 mmol) of 5-(3,4,5-trimethoxyphenyl)penta-(2E,4E)-dienoic acid and 155 mg (0.40 mmol) of 6-(N,N-dimethylamino)hexahydro-1,4-diazepine trihydrobromide synthesized by the process described in Referential Example 3. Added to a solution of 104 mg (0.16 mmol) of the resultant amorphous powder in ethanol (4 ml) was 0.30 ml (0.30 mmol) of 1N hydrochloric acid, and the mixture was concentrated under reduced pressure, thereby obtaining the title compound as a yellow amorphous powder.

H-NMR (DMSO-$d_6$, 120° C.) δ:
2.85(s,6H), 3.38–3.63(m,5H), 3.72(s,6H), 3.80(s,12H),
3.90–4.09(m,2H), 4.12–4.24(m,2H), 6.70(d,J=14.7 Hz,2H),
6.80(s,4H), 6.86(d,J=15.6 Hz,2H),
6.99(dd,J=15.6,10.4 Hz,2H), 7.26(dd,J=14.7,10.4 Hz,2H).

Example 44

Preparation of 1,4-bis[5-(2,3,4-trimethoxyphenyl)-penta-(2E,4E)-dienoyl]hexahydro-1,4-diazepine:

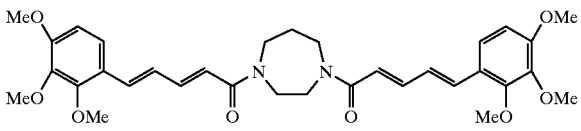

In accordance with the same process as in Example 41, 269 mg (yield: 86%) of crude crystals of the title compound were obtained from 308 mg (1.2 mmol) of 5-(2,3,4-trimethoxyphenyl)penta-(2E,4E)-dienoic acid and 53 mg (0.53 mmol) of homopiperazine. The crude crystals were recrystallized from ethyl acetate-hexane, thereby obtaining a pale yellow crystalline powder.

Melting point: 172–175° C.
$^1$H-NMR (DMSO-$d_6$, 120° C.) δ:
1.83(tt,J=5.9,5.9 Hz,2H), 3.57(dd,J=5.9,5.9 Hz,4H),
3.75–3.85(m,4H), 3.78(s,6H), 3.80(s,6H), 3.82(s,6H),
6.55(d,J=15.3 Hz,2H), 6.77(d,J=8.8 Hz,2H),
6.86–7.12(m,4H), 7.15–7.28(m,2H), 7.22(d,J=8.8 Hz,2H).

Example 45

Preparation of 1,4-bis[5-(3,4,5-trimethylphenyl)-penta-(2E,4E)-dienoyl]hexahydro-1,4-diazepine:

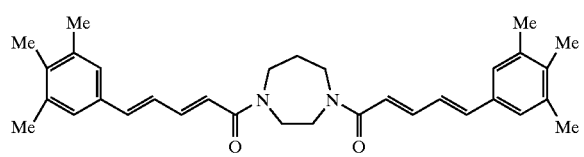

In accordance with the same process as in Example 41, 140 mg (yield: 56%) of the title compound was obtained as pale yellow amorphous powder from 238 mg (1.1 mmol) of 5-(3,4,5-trimethylphenyl)penta-(2E,4E)-dienoic acid and 50 mg (0.50 mmol) of homopiperazine.

$^1$H-NMR (DMSO-$d_6$, 120° C.) δ:
1.80(tt,J=5.8,5.8 Hz,2H), 2.12(s,6H), 2.22(s,12H),
3.56(dd,J=5.8,5.8 Hz,4H), 3.67(s,4H),
6.56(d,J=14.6 Hz,2H), 6.77(d,J=15.6 Hz,2H),
6.93(dd,J=15.6,10.5 Hz,2H), 7.09(s,4H),
7.20(dd,J=14.6,10.5 Hz,2H).

Example 46

Preparation of 1,4-bis[5-(4-tert-butyl-2-methoxy-phenyl)penta-(2E,4E)-dienoyl]-2-(N,N-dimethylaminomethyl)-piperazine hydrochloride:

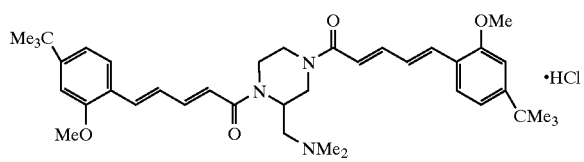

In accordance with the same process as in Example 41, 85 mg (yield: 68%) of 1,4-bis[5-(4-tert-butyl-2-methoxy-phenyl)penta-(2E,4E)-dienoyl]-2-(N,N-dimethylaminomethyl)-piperazine was obtained as a pale yellow amorphous powder from 114 mg (0.44 mmol) of 5-(4-tert-butyl-2-methoxy-phenyl)penta-(2E,4E)-dienoic acid and 50 mg (0.20 mmol) of 2-(N,N-dimethylaminomethyl)piperazine trihydrochloride synthesized by the process described in Referential Example 2.

Added to a solution of 85 mg (0.14 mmol) of the thus-obtained amorphous powder in ethanol (10 ml) was 0.30 ml (0.3 mmol) of 1N hydrochloric acid, and the resultant mixture was concentrated under reduced pressure, thereby obtaining the title compound as a pale yellow amorphous powder.

¹H-NMR (data for free base of the title compound) (DMSO-d₆, 120° C.) δ:
1.30(s,18H), 2.22(s,6H), 2.95–3.20(m,5H), 3.85(s,6H), 4.00–4.50(m,4H), 6.59(dd,J=14.5,4.2 Hz,2H), 6.85–7.15(m,8H), 7.26(dd,J=14.8,9.7 Hz,2H), 7.43(d,J=7.5 Hz,2H).

Example 47

Preparation of 1,4-bis[5-(2,6-dimethoxyphenyl)penta-(2E,4E)-dienoyl]-2-(N,N-dimethylaminomethyl)piperazine hydrochloride:

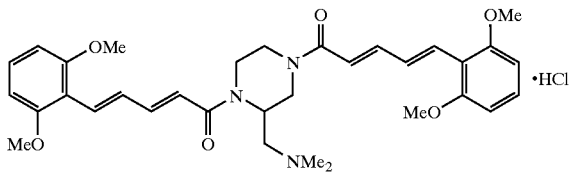

In accordance with the same process as in Example 41, 83 mg (yield: 53%) of 1,4-bis[5-(2,6-dimethoxyphenyl)penta-(2E,4E)-dienoyl]-2-(N,N-dimethylaminomethyl)piperazine was obtained as a pale yellow amorphous powder from 144 mg (0.62 mmol) of 5-(2,6-dimethoxyphenyl)penta-(2E,4E)-dienoic acid and 71 mg (0.28 mmol) of 2-(N,N-dimethylaminomethyl)-piperazine trihydrochloride synthesized by the process described in Referential Example 2.

Added to a solution of 83 mg (0.14 mmol) of the thus-obtained amorphous powder in ethanol (10 ml) was 0.30 ml (0.3 mmol) of 1N hydrochloric acid, and the resultant mixture was concentrated under reduced pressure, thereby obtaining the title compound as a pale yellow amorphous powder.

¹H-NMR (data for free base of the title compound) (DMSO-d₆, 120° C.) δ:
2.23(s,6H), 2.90–3.25(m,5H), 3.84(s,12H), 4.00–4.50(m,4H), 6.54(dd,J=14.0,3.9 Hz,2H), 6.67(d,J=8.5 Hz,4H), 7.15–7.35(m,8H).

Example 48

Preparation of N-[1,4-bis[5-(3,4,5-trimethoxy-phenyl) penta-(2E,4E)-dienoyl]-2-piperazinylmethyl]-phthalimide (in the formula, NPhth is a phthalimide group):

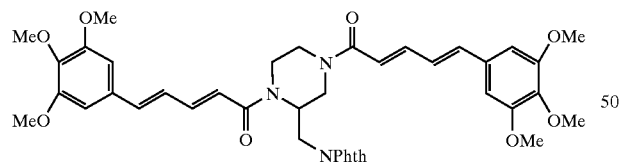

In accordance with the same process as in Example 41, 533 mg (yield: 75%) of the title compound was obtained as a pale yellow amorphous powder from 581 mg (2.2 mmol) of 5-(3,4,5-trimethoxyphenyl)penta-(2E,4E)-dienoic acid and 334 mg (1.0 mmol) of N-(2-piperazinylmethyl) phthalimide dihydrochloride synthesized by the same process as in Referential Example 2.

¹H-NMR (DMSO-d₆, 120° C.) (mixture of amide rotamers) δ:
2.91–3.55(m,5H), 3.61–3.75(m,6H), 3.75–3.91(m,12H), 3.99–4.38(m,3H), 4.72–4.88(m,1H), 6.35–6.51(m,2H), 6.52–7.02(m,9H), 7.29(dd,J=14.4,10.1 Hz,1H), 7.68–7.82(m,4H).

Example 49

Preparation of 2-aminomethyl-1,4-bis[5-(3,4,5-trimethoxyphenyl)penta-(2E,4E)-dienoyl]piperazine hydrochloride:

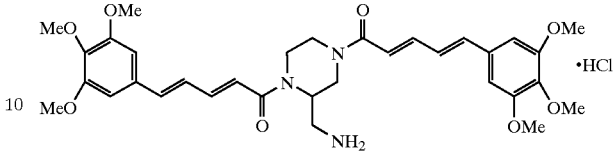

A solution of 1.3 ml (26 mmol) of hydrazine hydrate in methanol (2 ml) was added to a suspension of 430 mg (0.58 mmol) of N-[1,4-bis[5-(3,4,5-trimethoxyphenyl)penta-(2E, 4E)-dienoyl]-2-piperazinylmethyl]phthalimide synthesized by the process described in Example 48 in methanol (8 ml), and the mixture was stirred for 17 hours at room temperature. The reaction mixture was concentrated under reduced pressure, and the resultant residue was extracted with chloroform. An organic layer was washed with a saturated aqueous solution of sodium hydrogencarbonate and water, dried over anhydrous sodium sulfate, and then concentrated under reduced pressure. The resultant crude oil was purified by column chromatography on silica gel to obtain 232 mg (yield: 65%) of 2-aminomethyl-1,4-bis[5-(3,4,5-trimethoxyphenyl)penta-(2E,4E)-dienoyl]piperazine as a pale yellow amorphous powder.

Added to a solution of 93 mg (0.15 mmol) of the thus-obtained amorphous powder in ethanol (10 ml) was 0.30 ml (0.3 mmol) of 1N hydrochloric acid, and the resultant mixture was concentrated under reduced pressure, thereby obtaining the title compound as a pale yellow amorphous powder.

¹H-NMR (DMSO-d₆, 120° C.) δ:
(No N⁺H proton of the ammonium salt was observed)
3.03(br d,J=6.8 Hz,2H), 3.16–3.39(m,3H), 3.72(s,6H), 3.73(s,12H), 4.01–4.32(m,3H), 4.68–4.81(m,1H), 6.70(d,J=14.6 Hz,2H), 6.82(s,4H), 6.86(d,J=14.6 Hz,2H), 6.97(dd,J=14.6,10.2 Hz,2H), 7.28(dd,J=14.6,10.2 Hz,2H).

Referential Example 4

Preparation of 2,5-bis-tert-butoxycarbonyl-8-methyl-2,5, 8-triazabicyclo[4,3,0]nonane:

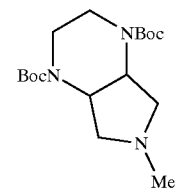

Added to a solution of 792 mg (12 mmol) of potassium hydroxide in water (38.5 ml) were 1.00 g (6.0 mmol) of pyrazine-2,3-dicarboxylic acid and 300 mg of 10% palladium on carbon, and the mixture was stirred for 16 hours at 50° C. under hydrogen. The catalyst was removed from the reaction mixture by suction filtration through Celite. A concentrated hydrochloric acid was added until the pH of the filtrate was 3, and the solution was concentrated under reduced pressure. Added to a solution of the resultant residue in methanol (20 ml) were 2.5 ml (18 mmol) of triethylamine and 4.0 g (18 mmol) of di-tert-butyl dicarbonate. After the resultant mixture was stirred for 30 minutes at room temperature, the reaction mixtur was concentrated under reduced pressure. Chloroform was added to the resultant residue, and the resultant solution was washed successively with water, 2N hydrochloric acid, and a saturated saline solution. An organic layer was dried over anhydrous sodium sulfate and then concentrated under reduced pressure, thereby obtaining 2.5 g of an oil containing 1,4-bis(tert-butoxycarbonyl)-piperazine-2,3-dicarboxylic acid.

Added to a solution of 2.5 g of the oil in xylene (20 ml) was 0.65 ml (5.9 mmol) of benzylamine, and the mixture was stirred and refluxed for 1 hour with continuous removal of water by a water separator. The reaction mixture was concentrated under reduced pressure, and the resultant residue was purified by column chromatography on silica gel, thereby obtaining 650 mg (yield: 25%) of 8-benzyl-2,5-bis-tert-butoxycarbonyl-2,5,8-triazabicyclo[4,3,0]nonane-7,9-dione as a colorless oil.

To a solution of 650 mg (1.5 mmol) of 8-benzyl-2,5-bis-tert-butoxycarbonyl-2,5,8-triazabicyclo-[4,3,0]nonane-7,9-dione in tetrahydrofuran (10 ml) was added 4N hydrogen chloride solution in ethyl acetate (10 ml) with stirring. After 30 minutes at 50° C., a 2.5N aqueous solution of sodium hydroxide (17 ml) was added to the reaction mixture, and the mixture was extracted with chloroform. An organic layer was dried over anhydrous sodium sulfate and then concentrated under reduced pressure. The resultant crude oil was purified by column chromatography on silica gel, thereby obtaining 85 mg (yield: 24%) of 8-benzyl-2,5,8-triazabicyclo[4,3,0]nonane-7,9-dione as a colorless oil.

To a solution of 80 mg (0.33 mmol) of 8-benzyl-2,5,8-triazabicyclo[4,3,0]nonane-7,9-dione in diethylene glycol dimethyl ether (1 ml) were added 38 mg (1.0 mmol) of sodium borohydride and 0.20 ml (1.6 mmol) of a boron trifluoride-diethyl ether complex with stirring for 2 hours at 70° C. under nitrogen. 6N Hydrochloric acid (0.53 ml) was added, and the mixture was stirred for 15 minutes a the same temperature. To the reaction mixture was added 242 mg (5.8 mmol) of sodium fluoride with stirring. After 30 minutes at 100° C., a 5N aqueous solution of sodium hydroxide (0.5 ml) was added, and the mixture was concentrated under reduced pressure. The resultant residue was extracted with diethyl ether, and an organic layer was dried over anhydrous sodium sulfate and then concentrated under reduced pressure, thereby obtaining 19 mg of a crude oil containing 8-benzyl-2,5,8-triazabicyclo-[4,3,0]nonane.

Added to a solution of 19 mg of this oil in tetrahydrofuran (1 ml) were 0.030 ml (0.22 mmol) of triethylamine and 44 mg (0.20 mmol) of di-tert-butyl dicarbonate. After the resultant mixture was stirred for 30 minutes at room temperature, the reaction mixture was concentrated under reduced pressure. The resultant residue was purified by preparative thin-layer chromatography on silica gel, thereby obtaining 39 mg (yield: 25%) of 8-benzyl-2,5-bis-tert-butoxycarbonyl-2,5,8-triazabicyclo-[4,3,0]nonane as a colorless oil.

To a solution of 39 mg (0.093 mmol) of 8-benzyl-2,5-bis-tert-butoxycarbonyl-2,5,8-triazabicyclo-[4,3,0]nonane synthesized by the above process in methanol (1.5 ml) were added 40 mg (0.63 mmol) of ammonium formate and 40 mg of 10% palladium on carbon. The mixture was stirred for 1 hour at 70° C. under nitrogen, and the catalyst was removed from the reaction mixture by suction filtration through Celite. The filtrate was concentrated under reduced pressure, and the resultant crude oil was purified by column chromatography on silica gel, thereby obtaining 29 mg (yield: 95%) of 2,5-bis-tert-butoxycarbonyl-2,5,8-triazabicyclo[4,3,0]nonane as a colorless oil.

Added to a solution of 29 mg of the thus obtained 2,5-bis-tert-butoxycarbonyl-2,5,8-triazabicyclo[4,3,0]-nonane in acetonitrile (0.7 ml) were 0.038 ml (0.51 mmol) of a 37% aqueous solution of formaldehyde and 9.4 mg (0.15 mmol) of sodium cyanoborohydride. After the mixture was stirred for 1 hour and 20 minutes at room temperature, acetic acid was added until the reaction mixture reached pH 4, and the resultant mixture was stirred for 30 minutes at room temperature. The reaction mixture was concentrated under reduced pressure, and the resultant crude oil was purified by column chromatography on silica gel, thereby obtaining 29 mg (yield: 96%) of the title compound as a colorless oil.

Example 50

Preparation of 2,5-bis[5-(3,4,5-trimethoxyphenyl)-penta-(2E,4E)-dienoyl]-8-methyl-2,5,8-triazabicyclo[4,3,0]-nonane hydrochloride:

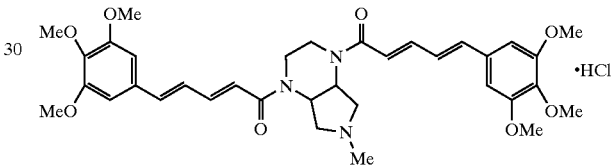

To a solution of 29 mg (0.085 mmol) of 2,5-bis-tert-butoxycarbonyl-8-methyl-2,5,8-triazabicyclo[4,3,0]nonane synthesized by the process described in Referential Example 4 in tetrahydrofuran (1 ml) was added 4N hydrogen chloride solution in ethyl acetate (1 ml) with stirring. After 30 minutes at room temperature, and another 30 minutes at 50° C., the reaction mixture was concentrated under reduced pressure, thereby obtaining 21 mg of an oil containing 8-methyl-2,5,8-triaza-bicyclo[4,3,0]nonane.

In accordance with the same process as in Example 41, 30 mg (yield: 56%) of 2,5-bis[5-(3,4,5-trimethoxyphenyl)-penta-(2E,4E)-dienoyl]-8-methyl-2,5,8-triazabicyclo[4,3,0]-nonane were obtained as a pale yellow amorphous powder from 21 mg of this oil and 58 mg (0.22 mmol) of 5-(3,4,5-trimethoxyphenyl)penta-(2E,4E)-dienoic acid.

Added to a solution of 30 mg (0.047 mmol) of the thus-obtained amorphous powder in ethanol (10 ml) was 0.10 ml (0.10 mmol) of 1N hydrochloric acid, and the resultant mixture was concentrated under reduced pressure, thereby obtaining the title compound as a pale yellow amorphous powder.

$^1$H-NMR (data for free base of the title compound) (DMSO-$d_6$, 120° C.) δ:

2.28(s,3H), 2.55–2.64(m,2H), 3.20–3.30(m,2H), 3.50–3.67(m,4H), 3.72(s,6H), 3.82(s,12H), 4.80–4.88(m,2H), 6.61(d,J=14.7 Hz,2H), 6.81(s,4H), 6.84(d,J=15.5 Hz,2H), 6.97(dd,J=15.5,10.4 Hz,2H), 7.27(dd,J=14.7,10.4 Hz,2H).

Example 51

Preparation of 4,8-bis[5-(3,4-dimethoxyphenyl)penta-(2E,4E)-dienoyl]-1,4,8-triazabicyclo[4,4,0]decane hydrochloride:

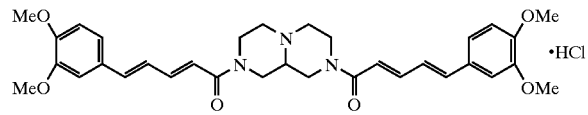

In accordance with the same process as in Example 41, 117 mg (yield: 72%) of 4,8-bis[5-(3,4-dimethoxyphenyl)-penta-(2E,4E)-dienoyl]-1,4,8-triazabicyclo[4,4,0]decane was obtained as a pale yellow amorphous powder from 146 mg (0.62 mmol) of 5-(3,4-dimethoxyphenyl)penta-(2E,4E)-dienoic acid and 40 mg (0.28 mmol) of 1,4,8-triazabicyclo[4,4,0]-decane[1].

Added to a solution of 117 mg (0.20 mmol) of the thus-obtained amorphous powder in ethanol (10 ml) was 0.40 ml (0.40 mmol) of 1N hydrochloric acid, and the resultant mixture was concentrated under reduced pressure to obtain crude crystals of the title compound. The crude crystals were recrystallized from methanol-diethyl ether, thereby obtaining a pale yellow crystalline powder.

(1) Gubert, S; Braojos, C; Sacristan, A; Ortiz, J. A., Synthesis, 1991, 318–320.
Melting point: 220° C. (decomposed).
$^1$H-NMR (DMSO-$d_6$, 120° C.) δ:
1.92(br dd,J=10.5,10.5 Hz,1H),
2.10(ddd,J=12.0,12.0,3.0 Hz,2H), 2.60–2.70(m,2H),
2.75–2.90(m,2H), 2.95–3.10(m,2H), 3.79(s,6H),
3.81(s,6H), 4.21(br d,J=10.5 Hz,4H),
6.62(d,J=14.7 Hz,2H), 6.83(br d,J=14.4 Hz,2H),
6.91(dd,J=14.4,8.7 Hz,2H), 6.93(d,J=8.3 Hz,2H),
7.04(dd,J=8.3,2.0 Hz,2H), 7.11(d,J=2.0 Hz,2H),
7.22(ddd,J=14.7,8.7,1.3 Hz,2H).

Example 52

Preparation of 4,8-bis[5-(3,4,5-trimethylphenyl)-penta-(2E,4E)-dienoyl]-1,4,8-triazabicyclo[4,4,0]decane hydrochloride:

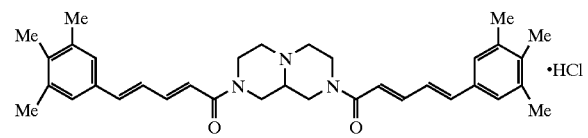

In accordance with the same process as in Example 41, 83 mg (yield: 66%) of 4,8-bis[5-(3,4,5-trimethylphenyl)-penta-(2E,4E)-dienoyl]-1,4,8-triazabicyclo[4,4,0]decane was obtained as a pale yellow amorphous powder from 111 mg (0.52 mmol) of 5-(3,4,5-trimethylphenyl)penta-(2E,4E)-dienoic acid and 33 mg (0.23 mmol) of 1,4,8-triazabicyclo-[4,4,0]-decane[1].

Added to a solution of 83 mg (0.15 mmol) of the thus-obtained amorphous powder in ethanol (10 ml) was 0.30 ml (0.30 mmol) of 1N hydrochloric acid, and the resultant mixture was concentrated under reduced pressure to obtain crude crystals of the title compound. The crude crystals were recrystallized from methanol-diethyl ether, thereby obtaining a pale yellow crystalline powder.

(1) Gubert, S.; Braojos, C.; Sacristan, A.; Ortiz, J. A., Synthesis, 1991, 318–320.
Melting point: 250° C. (decomposed).
$^1$H-NMR (DMSO-$d_6$, 120° C.) δ:
2.18(s,6H), 2.00–2.25(m,5H), 2.29(s,12H),
2.80–2.95(m,4H), 3.90–4.10(m,2H), 4.60–4.70(m,2H),
6.40(d,J=14.6 Hz,2H), 6.75–6.90(m,4H), 7.26(s,4H),
7.45(dd,J=15.8,10.6 Hz,2H).

Referential Example 5

Preparation of 3-(3,4-dihydro-6,7-dimethoxy-2-naphthyl)prop-(2E)-ene:

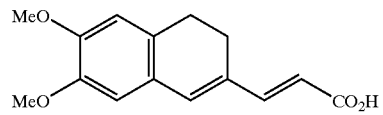

In accordance with the same process as in Referential Example 1, 1.25 g (65%) of crude crystals of the title compound were obtained from 1.60 g (7.4 mmol) of 3,4-dihydro-6,7-dimethoxy-2-naphthalenecarbaldehyde[1] and 2.20 g (9.7 mmol) of triethyl phosphonoacetate. The crude crystals was recrystallized from ethyl acetate, thereby obtaining pale yellow flakes.

(1) Narasimham, N. S.; Mukhopadhyay, T.; Kusurkar, S. S., Indian J. Chem., 1981, 20B, 546–548.
Melting point: 225–227° C.

Example 53

Preparation of 1,4-bis[3-(3,4-dihydro-6,7-dimethoxy-2-naphthyl)prop-(2E)-enoyl]hexahydro-1,4-diazepine:

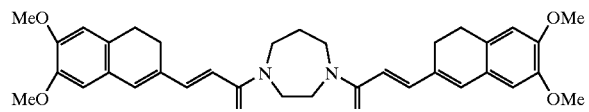

In accordance with the same process as in Example 41, 290 mg (yield: 97%) of crude crystals of the title compound were obtained from 292 mg (1.1 mmol) of 3-(3,4-dihydro-6,7-dimethoxy-2-naphthyl)prop-(2E)-enoic acid and 51 mg (0.51 mmol) of homopiperazine. The crude crystals were recrystallized from chloroform-hexane, thereby obtaining pale yellow crystalline powder.

Melting point: 255° C. (decomposed).
$^1$H-NMR (CDCl$_3$) (mixture of amide rotamers) δ:
2.10–2.95(m,2H), 2.43–2.57(m,4H),
2.86(br dd,J=8.0,8.0 Hz,4H), 3.60–4.00(m,8H),
3.88(s,6H), 3.90(s,6H), 6.28–6.41(m,2H),
6.65–6.74(m,6H), 7.47–7.63(m,2H).

Referential Example 6

Preparation of 3-(3,4-dihydro-6,7,8-trimethoxy-2-naphthyl)prop-(2E)-enoic acid:

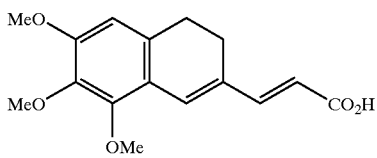

In accordance with the same process as in Referential Example 1, 308 mg (yield: 72%) of crude crystals of the title compound were obtained from 367 mg (1.5 mmol) of 3,4-dihydro-6,7,8-trimethoxy-2-naphthalenecarbaldehyde[1] and 404 mg (1.8 mmol) of triethyl phosphonoacetate. The crude crystals were recrystallized from ethyl acetate-hexane, thereby obtaining a pale yellow crystalline powder.

(1) Narasimham, N. S.; Mukhopadhyay, T.; Kusurkar, S. S., Indian J. Chem., 1981, 20B, 546–548.

Melting point: 191–194° C.

Example 54

Preparation of 1,4-bis[3-(3,4-dihydro-6,7,8-trimethoxy-2-naphthyl)prop-(2E)-enoyl]piperazine:

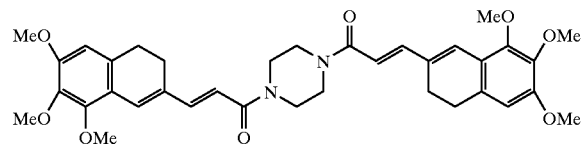

In accordance with the same process as in Example 41, 365 mg (quantitative) of crude crystals of the title compound were obtained from 370 mg (1.3 mmol) of 3-(3,4-dihydro-6,7,8-trimethoxy-2-naphthyl)prop-(2E)-enoic acid synthesized by the process described in Referential Example 6 and 50 mg (0.58 mmol) of piperazine. The crude crystals were recrystallized from chloroform-hexane, thereby obtaining a pale yellow crystalline powder.

Melting point: 241–244° C.

$^1$H-NMR (DMSO-$d_6$, 120° C.) δ:
2.48(dd,J=8.0,8.0 Hz,4H), 2.83(dd,J=8.0,8.0 Hz,4H), 3.60–3.80(m,8H), 3.86(s,6H), 3.89(s,6H), 3.91(s,6H), 6.35(d,J=15.1 Hz,2H), 6.52(s,2H), 7.04(s,2H), 7.57(d,J=15.1 Hz,2H).

Referential Example 7

Preparation of 3-(3,4-dihydro-5,6,7-trimethoxy-2-naphthyl)prop-(2E)-enoic acid:

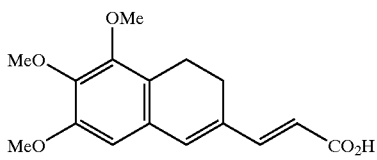

To 612 mg (8.4 mmol) of dimethylformamide was added 0.20 ml (2.1 mmol) of phosphorus oxychloride with stirring in an ice bath. The ice bath was removed and the reaction mixture was stirred at room temperature. After 5 minutes, 460 mg (2.1 mmol) of 3,4-dihydro-5,6,7-trimethoxy-naphthalene[1] was added to the resultant solution, and the resultant mixture was stirred for 10 minutes at 50° C. and for 3 hours at 80° C. A 2N aqueous solution of potassium acetate (6 ml) chilled with ice was added to the reaction mixture to conduct extraction with diethyl ether. An organic layer was washed with a saturated aqueous solution of sodium hydrogen-carbonate and a saturated saline solution, dried over anhydrous sodium sulfate and then concentrated under reduced pressure. The resultant crude oil (520 mg) was purified by column chromatography on silica gel, thereby obtaining 291 mg (yield: 56%) of 3,4-dihydro-5,6,7-trimethoxy-2-naphthalenecarbaldehyde as a colorless oil.

In accordance with the same process as in Referential Example 1, 173 mg (yield: 99%) of crude crystals of the title compound were obtained from 150 mg (0.60 mmol) of 3,4-dihydro-5,6,7-trimethoxy-2-naphthalenecarbaldehyde synthesized by the above process and 176 mg (0.79 mmol) of triethyl phosphonoacetate. The crude crystals were recrystallized from ethyl acetate-hexane, thereby obtaining a pale yellow crystalline powder.

(1) Haworth, R. D.; Moore, B. P.; Pauson, P. L., J. Chem. Soc., 1949, 3271–3278.

Melting point: 191–193° C.

Example 55

Preparation of 1,4-bis[3-(3,4-dihydro-5,6,7-trimethoxy-2-naphthyl)prop-(2E)-enoyl]hexahydro-1,4-diazepine:

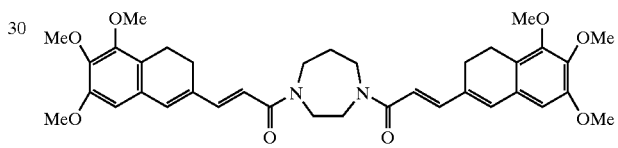

In accordance with the same process as in Example 41, 98 mg (yield: 76%) of crude crystals of the title compound were obtained from 131 mg (0.45 mmol) of 3-(3,4-dihydro-5,6,7-trimethoxy-2-naphthyl)prop-(2E)-enoic acid synthesized by the process described in Referential Example 7 and 20 mg (0.20 mmol) of homopiperazine. The crude crystals were recrystallized from chloroform-hexane, thereby obtaining a pale yellow crystalline powder.

Melting point: 176–179° C.

$^1$H-NMR (DMSO-$d_6$, 120° C.) δ:
1.80(tt,J=6.0,6.0 Hz,2H), 2.43(dd,J=8.1,8.1 Hz,4H), 2.74(dd,J=8.1,8.1 Hz,4H), 3.59(dd,J=6.0,6.0 Hz,4H), 3.71(s,4H), 3.75(s,6H), 3.77(s,6H), 3.78(s,6H), 6.50(d,J=15.1 Hz,2H), 6.62(s,2H), 6.67(s,2H), 7.22(d,J=15.1 Hz,2H).

Referential Example 8

Preparation of 3-(3,4-dihydro-4,4-dimethyl-5,6,7-trimethoxy-2-naphthyl)prop-(2E)-enoic acid:

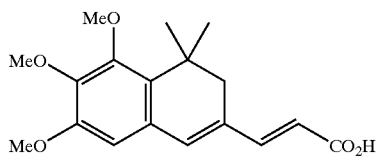

To anhydrous tetrahydrofuran (10 ml) stirred in an ice bath under nitrogen were added 104 mg (15 mmol) of lithium, 3.9 g (14 mmol) of 1-bromo-3-(3,4,5-trimethoxyphenyl)propane[1], and a solution of 0.95 ml (13 mmol) of acetone in tetrahydrofuran (10 ml). After the mixture was stirred for 17 hours at room temperature, a 2% aqueous solution of acetic acid (50 ml) chilled with ice was added to conduct extraction with diethyl ether. An organic layer was washed with a saturated aqueous solution of sodium hydrogencarbonate and a saturated saline solution, dried over anhydrous sodium sulfate and then concentrated under reduced pressure. The resultant crude oil (4.1 g) was purified by column chromatography on silica gel, thereby obtaining 860 mg (yield: 24%) of 2-methyl-5-(3,4,5-trimethoxyphenyl)pentan-2-ol.

To 908 mg (3.4 mmol) of 2-methyl-5-(3,4,5-trimethoxyphenyl)pentan-2-ol cooled in an ice bath was added 5 mg (80 mmol) of 85% sulfuric acid chilled with ice, and the mixture was stirred for 30 minutes. Ice water was added to the reaction mixture to conduct extraction with diethyl ether. An organic layer was washed with a saturated aqueous solution of sodium hydrogencarbonate and a saturated saline solution, dried over anhydrous sodium sulfate and then concentrated under reduced pressure, thereby obtaining 848 mg of a crude oil containing 1,1-dimethyl-1,2,3,4-tetrahydro-6,7,8-trimethoxynaphthalene.

Added to a solution of 848 mg (about 3.4 mmol) of this oil in carbon tetrachloride (45 ml) were 713 mg (4.0 mmol) of N-bromosuccinimide and 23 mg (0.095 mmol) of benzoyl peroxide, and the mixture was stirred for 3 hours at 85° C. The reaction mixture was washed with a saturated aqueous solution of sodium hydrogencarbonate and a saturated saline solution, dried over anhydrous sodium sulfate and then concentrated under reduced pressure. The resultant crude oil was purified by column chromatography on silica gel, thereby obtaining 430 mg (yield: 51%) of 3,4-dihydro-4,4-dimethyl-5,6,7-trimethoxy-naphthalene.

In accordance with the same process as in Referential Example 7, 81 mg (yield: 25%) of 3,4-dihydro-4,4-dimethyl-5,6,7-trimethoxy-2-naphthalenecarbaldehyde was synthesized from 294 mg (1.2 mmol) of 3,4-dihydro-4,4-dimethyl-5,6,7-trimethoxynaphthalene synthesized by the above process, and 95 mg (yield: 84%) of crude crystals of the title compound were then obtained from 98 mg (0.36 mmol) of 3,4-dihydro-4,4-dimethyl-5,6,7-trimethoxy-2-naphthalenecarbaldehyde. The crude crystals were recrystallized from diethyl ether-hexane, thereby obtaining pale yellow needles.
(1) Evans, D. A.; Tannis, S. P.; Hart. D. J., J. Am. Chem. Soc., 1981, 103, 5813–5821.
Melting point: 178–180° C.

Example 56

Preparation of 1,4-bis[3-(3,4-dihydro-4,4-dimethyl-5,6,7-trimethoxy-2-naphthyl)prop-(2E)-enoyl]hexahydro-1,4-diazepine:

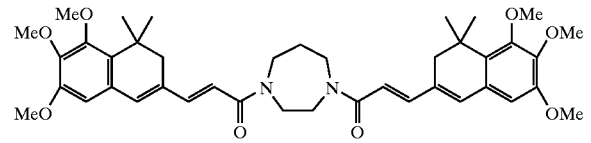

In accordance with the same process as in Example 41, 55 mg (yield: 58%) of crude crystals of the title compound were obtained from 95 mg (0.29 mmol) of 3-(3,4-dihydro-4,4-dimethyl-5,6,7-trimethoxy-2-naphthyl)prop-(2E)-enoic acid synthesized by the process described in Referential Example 8 and 14 mg (0.14 mmol) of homopiperazine. The crude crystals were recrystallized from ethyl acetate-hexane, thereby obtaining a pale yellow crystalline powder.

Melting point: 205–207° C.
$^1$H-NMR (DMSO-$d_6$, 120° C.) δ:
1.31(s,12H), 1.85(tt,J=6.0,6.0 Hz,2H), 2.31(s,4H), 3.60(dd,J=6.0,6.0 Hz,4H), 3.71(s,4H), 3.77(s,12H), 3.79(s,6H), 6.50(d,J=15.1 Hz,2H), 6.62(s,2H), 6.63(s,2H), 7.23(d,J=15.1 Hz,2H).

Referential Example 9

Preparation of 3-(6,7,8-trimethoxy-2-naphthyl)prop-(2E)-enoic acid:

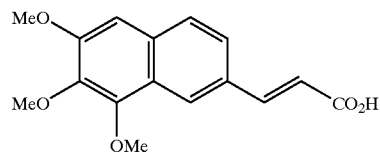

Added to a solution of 100 mg (0.34 mmol) of 3-(3,4-dihydro-6,7,8-trimethoxy-2-naphthyl)prop-(2E)-enoic acid synthesized by the process described in Referential Example 6 in toluene (2 ml) was 102 mg (0.41 mmol) of 2,3-dichloro-5,6-dicyano-p-benzoquinone, and the mixture was stirred for 1 hour and 30 minutes at 100° C. The reaction mixture was concentrated under reduced pressure, and the resultant crude oil was purified by column chromatography on silica gel, thereby obtaining 88 mg (yield: 88%) of crude crystals of the title compound. The crude crystals were recrystallized from chloroform-hexane, thereby obtaining a pale red crystalline powder.

Melting point: 199–201° C.

Example 57

Preparation of 1,4-bis[3-(6,7,8-trimethoxy-2-naphthyl)prop-(2E)-enoyl]hexahydro-1,4-diazepine:

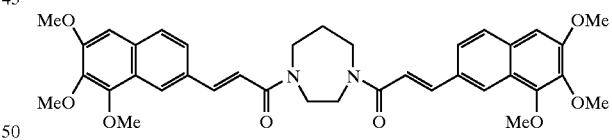

In accordance with the same process as in Example 41, 91 mg (yield: 71%) of crude crystals of the title compound were obtained from 152 mg (0.53 mmol) of 3-(6,7,8-trimethoxy-2-naphthyl)prop-(2E)-enoic acid synthesized by the process described in Referential Example 9 and 20 mg (0.20 mmol) of homopiperazine. The crude crystals were recrystallized from methanol-diethyl ether, thereby obtaining a pale brown crystalline powder.

Melting point: 199–204° C.
$^1$H-NMR (CDCl$_3$) (mixture of amide rotamers) δ:
2.00–2.20(m,2H), 3.70–3.80(m,4H), 3.80–3.90(m,4H), 3.98(s,6H), 3.99(s,6H), 4.07(s,3H), 4.08(s,3H), 6.92(d,J=15.0 Hz;2H), 6.95(s,2H), 7.60–7.75(m,4H), 7.80–8.00(m,2H), 8.14(s,2H).

Referential Example 10

Preparation of 3-(5,6,7-trimethoxy-2-naphthyl)prop-(2E)-enoic acid:

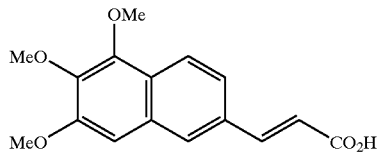

In accordance with the same process as in Referential Example 9, 241 mg (yield: 99%) of crude crystals of the title compound were obtained from 264 mg (0.85 mmol) of 3-(3,4-dihydro-5,6,7-trimethoxy-2-naphthyl)prop-(2E)-enoic acid synthesized by the process described in Referential Example 7. The crude crystals were recrystallized from chloroform-hexane, thereby obtaining a pale red crystalline powder.

Melting point: 169–170° C.

Example 58

Preparation of 1,4-bis[3-(5,6,7-trimethoxy-2-naphthyl)prop-(2E)-enoyl]hexahydro-1,4-diazepine:

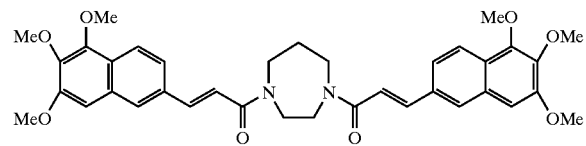

In accordance with the same process as in Example 41, 66 mg (yield: 44%) of crude crystals of the title compound were obtained from 108 mg (0.37 mmol) of 3-(5,6,7-trimethoxy-2-naphthyl)prop-(2E)-enoic acid synthesized by the process described in Referential Example 10 and 17 mg (0.17 mmol) of homopiperazine. The crude crystals were recrystallized from ethyl acetate-hexane, thereby obtaining a pale brown crystalline powder.

Melting point: 170–176° C.

$^1$H-NMR (DMSO-$d_6$, 120° C.) δ:

1.90(tt,J=6.1,6.1 Hz,2H), 3.69(dd,J=6.1,6.1 Hz,4H),
3.82(s,4H), 3.88(s,6H), 3.91(s,6H), 3.96(s,6H),
7.10(s,2H), 7.11(d,J=15.3 Hz,2H), 7.56(d,J=15.3 Hz,2H),
7.59(dd,J=8.5,1.5 Hz,2H), 7.88(d,J=8.5 Hz,2H),
7.89(br s,2H).

Referential Example 11

Preparation of 3-(5,6-dimethoxy-3,3-dimethyl-2-indenyl)prop-(2E)-enoic acid:

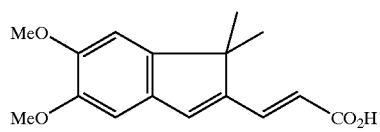

To anhydrous tetrahydrofuran (35 ml) stirred in an ice bath under nitrogen were added 503 mg (70 mmol) of lithium, 7.84 g (32 mmol) of 1-bromo-2-(3,4-dimethoxyphenyl)ethane[1], and a solution of 2.3 ml (32 mmol) of acetone in tetrahydrofuran (70 ml). After the mixture was stirred for 2 hours at room temperature, a 1N aqueous solution of acetic acid (100 ml) chilled with ice was added to conduct extraction with diethyl ether. An organic layer was washed with a saturated aqueous solution of sodium hydrogencarbonate and a saturated saline solution, dried over anhydrous sodium sulfate and then concentrated under reduced pressure. The resultant crude oil was purified by column chromatography on silica gel, thereby obtaining 3.4 g (yield: 47%) of 4-(3,4-dimethoxyphenyl)-2-methylbutan-2-ol as a colorless oil.

To 3.5 g (16 mmol) of 4-(3,4-dimethoxyphenyl)-2-methylbutan-2-ol cooled in an ice bath was added 20 ml (320 mmol) of 85% sulfuric acid chilled with ice, and the mixture was stirred for 30 minutes. Ice water was then added to the reaction mixture to conduct extraction with diethyl ether. An organic layer was washed with a saturated aqueous solution of sodium hydrogencarbonate and a saturated saline solution, dried over anhydrous sodium sulfate and then concentrated under reduced pressure, thereby obtaining 2.6 g of a crude oil containing 5,6-dimethoxy-1,1-dimethylindane.

Added to a solution of 2.6 g (about 13 mmol) of this oil in benzene (96 ml) were 13.7 g (64 mmol) of pyridinium chlorochromate and 31.8 g of Celite, and the mixture was stirred for 1 hour at 85° C. Insoluble materials were removed from the reaction mixture by suction filtration through Celite, and the residue on Celite was washed with diethyl ether and ethyl acetate. The filtrate and washings were combined and concentrated under reduced pressure. The resultant crude oil was purified by column chromatography on silica gel, thereby obtaining 2.1 g (yield: 77%) of 5,6-dimethoxy-3,3-dimethylindan-1-one as a colorless oil.

Then, 1.1 g (28 mmol) of sodium borohydride were added to a solution of 1.9 g (9.2 mmol) of 5,6-dimethoxy-3,3-dimethylindan-1-one in methanol (30 ml), and the mixture was stirred for 5 minutes at room temperature. After methanol was removed from the reaction mixture by concentration under reduced pressure, water was added to the residue, and the mixture was extracted with diethyl ether. An organic layer was washed with a saturated saline solution, dried over anhydrous sodium sulfate and then concentrated under reduced pressure. Added to a solution of the resultant residue in toluene (50 ml) was 90 mg (0.47 mmol) of p-toluenesulfonic acid monohydrate, and the mixture was stirred for 20 minutes at 120° C. The reaction mixture was concentrated under reduced pressure, and the resultant crude oil was purified by column chromatography on silica gel to obtain 264 mg (yield: 15%) of 5,6-dimethoxy-1,1-dimethylindene as a colorless oil.

In accordance with the same process as in Referential Example 7, 260 mg (yield: 99%) of 5,6-dimethoxy-1,1-dimethyl-2-indenecarbaldehyde was synthesized from 264 mg (1.3 mmol) of 5,6-dimethoxy-1,1-dimethylindene synthesized by the above process, and 177 mg (yield: 50%) of crude crystals of the title compound were then obtained from 299 mg (1.3 mmol) of 5,6-dimethoxy-1,1-dimethyl-2indenecarbaldehyde. The crude crystals were recrystallized from diethyl ether-hexane, thereby obtaining a pale yellow crystalline powder.

(1) Kuhn, H.; Liao, Zeng-Kun, J. Org. Chem., 1982, 47, 2787–2789.

Melting point: 177–180° C.

Example 59

Preparation of 1,4-bis[3-(5,6-dimethoxy-1,1-dimethyl-2-indenyl)prop-(2E)-enoyl]hexahydro-1,4-diazepine:

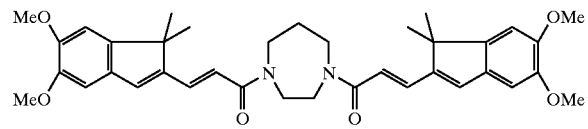

In accordance with the same process as in Example 41, 69 mg (yield: 66%) of crude crystals of the title compound were obtained from 103 mg (0.37 mmol) of 3-(5,6-dimethoxy-1,1-dimethyl-2-indenyl)prop-(2E)-enoic acid synthesized by the process described in Referential Example 11 and 17 mg (0.17 mmol) of homopiperazine. The crude crystals were recrystallized from ethyl acetate-hexane, thereby obtaining a pale yellow crystalline powder.

Melting point: 203–207° C.
$^1$H-NMR (DMSO-$d_6$, 120° C.) δ:
1.32(s,12H), 1.85(tt,J=6.0,6.0 Hz,2H),
3.64(dd,J=6.0,6.0 Hz,4H), 3.75(s,4H), 3.77(s,6H),
3.82(s,6H), 6.63(d,J=15.6 Hz,2H), 6.97(s,2H),
6.99(s,2H), 7.04(s,2H), 7.31(d,J=15.6 Hz,2H).

Referential Example 12

Preparation of 3-(1,1-dimethyl-5,6,7-trimethoxy-2-indenyl)prop-(2E)-enoic acid:

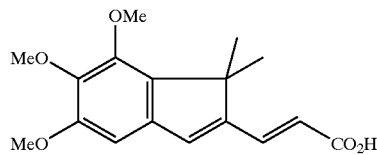

The following conversion was conducted in accordance with the same process as in Referential Example 8. First, 1.43 g (yield: 46%) of 2-methyl-4-(3,4,5-trimethoxyphenyl)-butan-2-ol was synthesized from 3.34 g (12 mmol) of 1-bromo-2-(3,4,5-trimethoxyphenyl)-ethane[1]. Then, 484 mg (yield: 37%) of 1,1-dimethyl-5,6,7-trimethoxyindene was obtained from 1.43 g (5.6 mmol) of 2-methyl-4-(3,4,5-trimethoxyphenyl)butan-2-ol, and 60 mg (yield: 14%) of 1,1-dimethyl-5,6,7-trimethoxy-2-indenecarbaldehyde were obtained from 379 mg (1.6 mmol) of 1,1-dimethyl-5,6,7-trimethoxyindene. Finally, 81 mg (quantitative) of crude crystals of the title compound were obtained from 70 mg (0.27 mmol) of 1,1-dimethyl-5,6,7-trimethoxy-2-indenecarbaldehyde. The crude crystals were recrystallized from ethyl acetate-hexane, thereby obtaining a pale yellow crystalline powder.

(1) Dean, R. T.; Rapport, H., J. Org. Chem., 1978, 43, 2115–2122.

Melting point: 175–176° C.

Example 60

Preparation of 1,4-bis[3-(1,1-dimethyl-5,6,7-trimethoxy-2-indenyl)prop-(2E)-enoyl]hexahydro-1,4-diazepine:

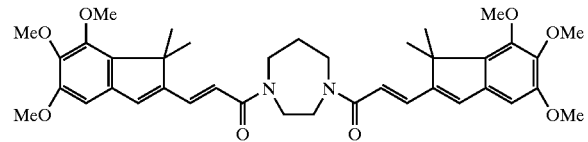

In accordance with the same process as in Example 41, 58 mg (yield: 72%) of crude crystals of the title compound were obtained from 80 mg (0.26 mmol) of 3-(1,1-dimethyl-5,6,7-trimethoxy-2-indenyl)prop-(2E)-enoic acid synthesized by the process described in Referential Example 12 and 12 mg (0.12 mmol) of homopiperazine. The crude crystals were recrystallized from ethyl acetate-hexane, thereby obtaining a pale yellow crystalline powder.

Melting point: 176–179° C.
$^1$H-NMR (DMSO-$d_6$, 120° C.) δ:
1.39(s,12H), 1.83(tt,J=6.1,6.1 Hz,2H),
3.63(dd,J=6.1,6.1 Hz,4H), 3.75(s,4H), 3.78(s,6H),
3.80(s,6H), 3.90(s,6H), 6.68(d,J=15.6 Hz,2H),
6.78(s,2H), 6.94(s,2H), 7.25(d,J=15.6 Hz,2H).

Example 61

Preparation of 4,8-bis[5-(3,4,5-trimethoxyphenyl)-penta-(2E,4E)-dienoyl]-1,4,8-triazabicyclo[4,4,0]decane hydrochloride:

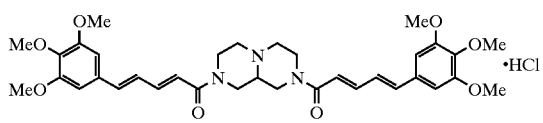

In accordance with the same process as in Example 41, 4,8-bis[5-(3,4,5-trimethoxyphenyl)penta-(2E,4E)-dienoyl]-1,4,8-triazabicyclo[4,4,0]decane was obtained as a pale yellow amorphous powder from 290 mg (1.1 mmol) of 5-(3,4,5-trimethoxyphenyl)penta-(2E,4E)-dienoic acid and 70 mg (0.50 mmol) of 1,4,8-triazabicyclo [4,4,0]decane[1]. Added to a solution of the thus-obtained amorphous powder in ethanol (30 ml) was 0.10 ml (1.2 mmol) of concentrated hydrochloric acid, and the resultant mixture was concentrated under reduced pressure to obtain crude crystals of the title compound. The crude crystals were recrystallized from methanol-chloroform-diethyl ether, thereby obtaining 199 mg (yield: 60%) of the title compound as a pale yellow crystalline powder.

(1) Gubert, S.; Braojos, C.; Sacristan, A.; Ortiz, J. A., Synthesis, 1991, 318–320.

Melting point: 190° C. (decomposed).
$^1$H-NMR (DMSO-$d_6$, 120° C.) (no N$^+$H proton of the ammonium salt was observed) δ:
2.55–2.85(m,3H), 2.95–3.10(m,2H),
3.19(br d,J=8.5 Hz,2H), 3.32(br dd,J=8.5,8.5 Hz,2H),
3.73(s,6H), 3.82(s,12H), 4.31(br d,J=13.5 Hz,2H),
4.37(br d,J=13.5 Hz,2H), 6.68(d,J=14.6 Hz,2H),
6.81(s,4H), 6.87(d,J=15.6 Hz,2H),
6.96(dd,J=15.6,10.5 Hz,2H), 7.26(dd,J=14.6,10.5 Hz,2H).

Referential Example 13

Preparation of ethyl 3-(3,4-dihydro-6,7-dimethoxy-2-naphthyl)-2-propynoate:

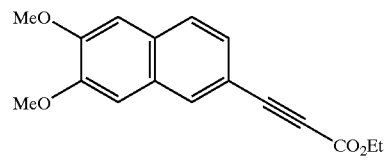

A solution of 245 mg (1.2 mmol) of 6,7-dimethoxy-2-tetralone in anhydrous tetrahydrofuran (2.0 ml) was added to 2.9 ml (1.5 mmol) of a 0.50 M tetrahydrofuran solution of lithium diisopropylamide while stirring at −78° C. under nitrogen, and the mixture was stirred for 45 minutes. Thereafter, a solution of 562 mg (1.6 mmol) of N-phenyl-trifluoromethanesufonimide in tetrahydrofuran (3.0 ml) was added. After stirring the mixture for 15 minutes at −78° C., the reaction vessel was transferred to an ice bath, and stirring was conducted for 30 minutes. The reaction mixture was concentrated under reduced pressure, and the resultant crude oil was purified by column chromatography on silica gel to obtain 334 mg (yield: 83%) of 3,4-dihydro-6,7-dimethoxy-2-naphthyl-trifluoromethanesulfonate as a colorless oil.

To a solution of 178 mg (0.53 mmol) of (3,4-dihydro-6,7-dimethoxy-2-naphthyl) trifluoromethane-sulfonate in dimethylformamide (2 ml) were added 0.39 ml (3.9 mmol) of ethyl 2-propynoate, 84.8 mg (1.0 mmol) of sodium acetate and 14.8 mg (0.020 mmol) of bis(triphenylphosphine)-palladium (II) acetate with stirring under nitrogen, and the mixture was stirred for 1 hour and 30 minutes at 60° C. A saturated saline solution was added to the reaction mixture to conduct extraction with benzene-hexane (1:2). An organic layer was washed with a saturated saline solution, dried over anhydrous sodium sulfate and then concentrated under reduced pressure. The resultant crude oil was purified by column chromatography on silica gel to obtain 76.5 mg (yield: 51%) of crude crystals of the title compound. The crude crystals were recrystallized from diethyl ether-hexane, thereby obtaining a pale yellow crystalline powder.

Melting point: 98.5–99.5° C.

Example 62

Preparation of 1,4-bis[3-(3,4-dihydro-6,7-dimethoxy-2-naphthyl)-2-propynoyl]hexahydro-1,4-diazepine:

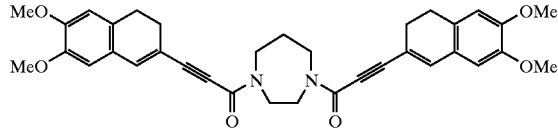

Added to a solution of 65.2 mg (0.23 mmol) of ethyl 3-(3,4-dihydro-6,7-dimethoxy-2-naphthyl)-2-propynoate synthesized by the process described in Referential Example 13 in methanol-tetrahydrofuran (1:1; 1 ml) was 0.5 ml (2.5 mmol) of a 5N aqueous solution of potassium hydroxide, and the mixture was stirred for 30 minutes at room temperature. A saturated saline solution and 0.25 ml (3.0 mmol) of concentrated hydrochloric acid were added to the reaction mixture to conduct extraction with chloroform. An organic layer was dried over anhydrous sodium sulfate and then concentrated under reduced pressure. The resultant concentrated residue was purified by column chromatography on silica gel to obtain 61.4 mg (quantitative) of 3-(3,4-dihydro-6,7-dimethoxy-2-naphthyl)-2-propynoic acid as a colorless amorphous powder.

In accordance with the same process as in Example 33, crude crystals of the title compound were obtained from 61.4 mg (0.24 mmol) of 3-(3,4-dihydro-6,7-dimethoxy-2-naphthyl)-2-propynoic acid synthesized by the above process and 11.9 mg (0.12 mmol) of homopiperazine. The crude crystals were recrystallized from chloroform-hexane, thereby obtaining 30.5 mg (yield: 44%) of a pale yellow crystalline powder.

Melting point: 246–247° C.

$^1$H-NMR (DMSO-$d_6$, 120° C.) (mixture of amide rotamers) δ:
1.60–2.05(m,1H), 2.35–2.55(m,4H), 2.70–2.90(m,4H), 3.50–4.00(m,20H), 6.69(br s,2H), 6.79(br s,2H), 6.96(br s,2H).

Example 63

Preparation of 1,4-bis[3-(2-naphthyl)prop-(2E)-enoyl]hexahydro-1,4-diazepine:

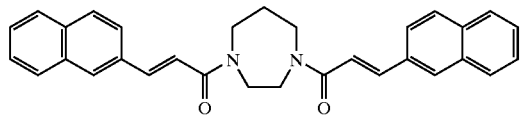

In accordance with the same process as in Example 33, crude crystals of the title compound were obtained from 224 mg (1.1 mmol) of 3-(2-naphthyl)prop-(2E)-enoic acid and 51.6 mg (0.52 mmol) of homopiperazine. The crude crystals were recrystallized from chloroform-diethyl ether, thereby obtaining 200 mg (yield: 84%) of a colorless crystalline powder.

Melting point: 200–201° C.

$^1$H-NMR (DMSO-$d_6$, 120° C.) δ:
1.90(tt,J=5.9,5.9 Hz,2H), 3.70(dd,J=5.9,5.9 Hz,4H), 3.83(s,4H), 7.17(d,J=15.5 Hz,2H), 7.44–7.53(m,4H), 7.61(d,J=15.5 Hz,2H), 7.73–7.89(m,8H), 8.03(br s, 2H).

Example 64

Preparation of 1,4-bis[3-(3-quinolyl)prop-(2E)-enoyl]hexahydro-1,4-diazepine:

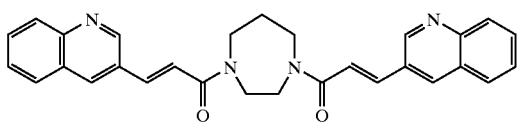

In accordance with the same process as in Example 33, crude crystals of the title compound were obtained from 230 mg (0.98 mmol) of 3-(3-quinolyl)prop-(2E)-enoic acid hydrochloride and 39.9 mg (0.40 mmol) of homopiperazine. The crude crystals were recrystallized from chloroform-diethyl ether, thereby obtaining 177 mg (yield: 96%) of a colorless crystalline powder.

Melting point: 274–276° C.

$^1$H-NMR (DMSO-$d_6$, 120° C.) δ:
1.91(tt,J=6.0,6.0 Hz,2H), 3.72(dd,J=6.0,6.0 Hz,4H), 3.85(s,4H), 7.35(d,J=15.6 Hz,2H), 7.56(br dd,J=8.0,6.9 Hz,2H), 7.64(br d,J=15.6 Hz,2H), 7.71(ddd,J=8.5,6.9,1.5 Hz,2H), 7.88(br d,J=8.0 Hz,2H), 7.97(br d,J=8.5 Hz,2H), 8.46(br s,2H), 9.15(d,J=2.2 Hz,2H).

Referential Example 14

Preparation of 3-(3,4,5-trimethoxyphenyl)-2-propynoic acid[1]:

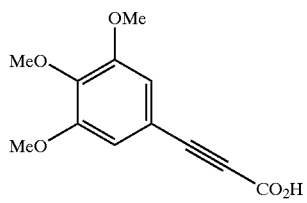

To a solution of 2.36 g (8.0 mmol) of 1-iodo-3,4,5-trimethoxybenzene[2] in triethylamine (80 ml) were added 1.38 ml (9.6 mmol) of 3,3-diethoxy-1-propane, 56 mg (0.080 mmol) of bis(triphenylphosphine)palladium (II) chloride and 8.0 mg (0.040 mmol) of cuprous iodide with stirring under nitrogen, and the mixture was stirred for 3 hours at room temperature. Insoluble materials were removed from the reaction mixture by suction filtration through Celite, and the filtrate was concentrated under reduced pressure. The resultant crude oil was purified by column chromatography on silica gel to obtain 2.29 g (yield: 97%) of 1,1-diethoxy-3-(3,4,5-trimethoxyphenyl)-2-propyne as colorless needles (melting point: 62.5–63.0° C.).

Added to a solution of 2.0 g (6.8 mmol) of 1,1-diethoxy-3-(3,4,5-trimethoxyphenyl)-2-propyne in acetonitrile (30 ml) was 10 ml (60 mmol) of 6N sulfuric acid, and the mixture was stirred for 1 hour at room temperature. After the reaction mixture was concentrated under reduced pressure to remove acetonitrile, the residue was extracted with ethyl acetate. An organic layer was washed with a saturated saline solution, dried over anhydrous sodium sulfate and then concentrated under reduced pressure. The resultant crude oil was purified by column chromatography on silica gel to obtain 1.42 g (yield: 95%) of crude crystals of 3-(3,4,5-trimethoxyphenyl)-2-propyn-1-al. The crude crystals were recrystallized from chloroform-hexane, thereby obtaining colorless needles (melting point: 95.5–96.0° C.).

To a solution of 480 mg (2.2 mmol) of 3-(3,4,5-trimethoxyphenyl)-2-propyn-1-al in tert-butyl alcohol (25 ml) cooled in an ice bath were added 15 ml (15 mmol) of a 1 M aqueous solution of sodium dihydrogenphosphate and 1.96 g (22 mmol) of sodium chlorite, and the mixture was stirred for 3 hours. To the reaction mixture was added 2 ml (24 mmol) of concentrated hydrochloric acid and the mixture was extracted with chloroform. An organic layer was washed with a 10% aqueous solution of sodium thiosulfate acidified with hydrochloric acid, dried over anhydrous sodium sulfate and then concentrated under reduced pressure. The resultant residue was recrystallized from diethyl ether-hexane, thereby obtaining 427 mg (yield: 83%) of the title compound as a colorless crystalline powder.

(1) Klemm, L. H.; Gopinath, K. W.; Karaboyas, G. C.; Capp, G. L.; Lee. D. H., Tetrahedron 1964, 20, 871–876.
(2) Bacon, R. G. R.; Wright, J. R., J. Chem. Soc. 1969, 1978–1981

Example 65

Preparation of 1,4-bis[3-(3,4,5-trimethoxyphenyl)-2-propynoyl]hexahydro-1,4-diazepine:

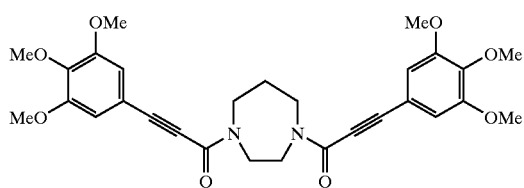

In accordance with the same process as in Example 33, crude crystals of the title compound were obtained from 80 mg (0.34 mmol) of 3-(3,4,5-trimethoxyphenyl)-2-propynoic acid[1] synthesized by the process described in Referential Example 14 and 16 mg (0.16 mmol) of homopiperazine. The crude crystals were recrystallized from acetone-diethyl ether, thereby obtaining 41 mg (yield: 48%) of a colorless crystalline powder.

(1) Klemm, L. H.; Gopinath, K. W.; Karaboyas, G. C.; Capp, G. L.; Lee. D. H., Tetrahedron, 1964, 20, 871–876.
Melting point: 197–198° C.

$^1$H-NMR (DMSO-$d_6$, 120° C.) (mixture of amide rotamers) δ:

1.72–2.12(m,2H), 1.98–2.08(m,4H), 3.55–4.07(m,4H), 3.67–3.90(m,18H), 6.66–6.92(m,4H).

Example 66

Preparation of 4,8-bis[3-(3,4,5-trimethoxyphenyl)-2-propynoyl]-1,4,8-triazabicyclo[4,4,0]decane:

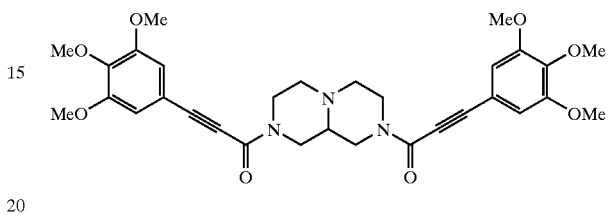

In accordance with the same process as in Example 33, crude crystals of the title compound were obtained from 80 mg (0.34 mmol) of 3-(3,4,5-trimethoxyphenyl)-2-propynoic acid[1] synthesized by the process described in Referential Example 14 and 23 mg (0.16 mmol) of 1,4,8-triazabicyclo-[4,4,0]decane[2]. The crude crystals were recrystallized from acetone-diethyl ether, thereby obtaining 36 mg (yield: 39%) of a colorless crystalline powder.

(1) Klemm, L. H.; Gopinath, K. W.; Karaboyas, G. C.; Capp, G. L.; Lee. D. H., Tetrahedron, 1964, 20, 871–876.
(2) Gubert, S.; Braojos, C.; Sacristan, A.; Ortiz, J. A. Synthesis, 1991, 318–320.
Melting point: 210–211° C.

$^1$H-NMR (DMSO-$d_6$, 120° C.) (mixture of amide rotamers) δ:

1.98–2.08(m,1H), 2.12–2.26(m,2H), 2.43–2.50(m,2H), 2.64–2.80(m,2H), 2.83–2.92(m,2H), 3.72–3.86(m,18H), 4.22–4.40(m,4H), 6.78–6.87(m,4H).

Referential Example 15

Preparation of 5-(3,4,5-trimethoxyphenyl)pent-(2E)-en-4-ynoic acid:

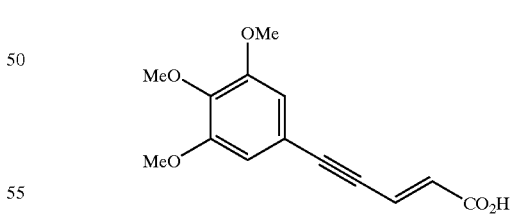

In accordance with the same process as in Referential Example 1, 205 mg (yield: 97%) of crude crystals of the title compound were obtained from 176 mg (0.80 mmol) of 3-(3,4,5-trimethoxyphenyl)-2-propyn-1-al synthesized by the process described in Referential Example 14 and 235 mg (1.1 mmol) of triethyl phosphonoacetate. The crude crystals were recrystallized from ethyl acetate, thereby obtaining pale yellow needles.

Melting point: 125° C. (decomposed).

Example 67

Preparation of 1,4-bis[5-(3,4,5-trimethoxyphenyl)-pent-(2E)-en-4-ynoyl]hexahydro-1,4-diazepine:

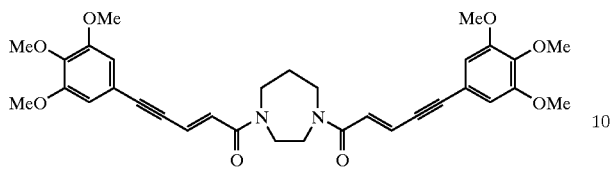

In accordance with the same process as in Example 33, crude crystals of the title compound were obtained from 162 mg (0.61 mmol) of 5-(3,4,5-trimethoxyphenyl)pent-(2E)-en-4-ynoic acid synthesized by the process described in Referential Example 15 and 30 mg (0.30 mmol) of homopiperazine. The crude crystals were recrystallized from ethyl acetate-diethyl ether-hexane, thereby obtaining 143 mg (yield: 81%) of a pale yellow crystalline powder.

Melting point: 191–193° C.

$^1$H-NMR (CdCl$_3$, 120° C.) (mixture of amide rotamers) δ: 1.94–2.07(m,2H), 3.54–3.82(m,8H), 3.87(s,18H), 6.69–6.88(m,6H), 6.95–7.12(m,2H).

Example 68

Preparation of 4,8-bis[5-(3,4,5-trimethoxyphenyl)-pent-(2E)-en-4-ynoyl]-1,4,8-triazabicyclo[4,4,0]decane hydrochloride:

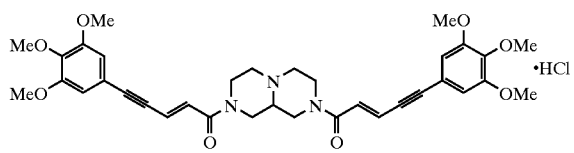

In accordance with the same process as in Example 33, 77 mg (yield: 61%) of 4,8-bis[5-(3,4,5-trimethoxyphenyl)-pent-(2E)-en-4-ynoyl]-1,4,8-triazabicyclo[4,4,0]decane was obtained as a pale yellow amorphous powder from 110 mg (0.42 mmol) of 5-(3,4,5-trimethoxyphenyl)pent-(2E)-en-4-ynoic acid synthesized by the process described in Referential Example 15 and 28 mg (0.20 mmol) of 1,4,8-triazabicyclo[4,4,0]decane[1].

Added to a solution of 77 mg (0.12 mmol) of the thus-obtained amorphous powder in ethanol (10 ml) were 0.25 ml (0.25 mmol) of 1N hydrochloric acid, and the resultant mixture was concentrated under reduced pressure to obtain crude crystals of the title compound. The crude crystals were recrystallized from ethanol-diethyl ether, thereby obtaining a pale yellow crystalline powder.

(1) Gubert, S.; Braojos, C.; Sacristan, A.; Ortiz, J. A., Synthesis, 1991, 318–320.

Melting point: 229–231° C.

$^1$H-NMR (DMSO-d$_6$, 120° C.) δ:
2.45–2.65(m,4H), 2.80–3.35(m,8H), 3.74(s,6H),
3.79(s,12H), 4.25–4.40(m,1H), 6.77(s,4H),
6.83(d,J=15.1 Hz,2H), 7.04(d,J=15.1 Hz,2H).

Referential Example 16

Preparation of 4-(3,4,5-trimethoxyphenyl)benzoic acid:

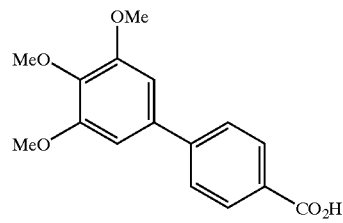

To a solution of 137 mg (0.60 mmol) of ethyl 4-bromobenzoate in toluene (1.4 ml) were added a solution of 152 mg (0.72 mmol) of 3,4,5-trimethoxyphenylboronic acid[1] in methanol (0.7 ml), 21 mg (0.018 mmol) of tetrakis-(triphenylphosphine)palladium, and 0.70 ml (1.4 mmol) of a 2 M aqueous solution of potassium carbonate with stirring under nitrogen, and the mixture was stirred for 5 hours at 80° C. The reaction mixture was concentrated under reduced pressure, and the residue was dissolved in methanol (1.0 ml). To the solution was added 1.0 ml (5.0 mmol) of a 5N aqueous solution of sodium hydroxide. After stirring for 2 hours at 70° C., the reaction mixture was concentrated under reduced pressure to remove methanol, and water was added to the residue to conduct extraction with chloroform. An organic layer was washed with a saturated saline solution, dried over anhydrous sodium sulfate and then concentrated under reduced pressure, thereby obtaining crude crystals. The crude crystals were recrystallized from chloroform-hexane, thereby obtaining 170 mg (yield: 99%) of the title compound as a colorless crystalline powder.

Melting point: 160–164° C.

(1) WO96/26195.

Example 69

Preparation of 1,4-bis[4-(3,4,5-trimethoxyphenyl)-benzoyl]hexahydro-1,4-diazepine:

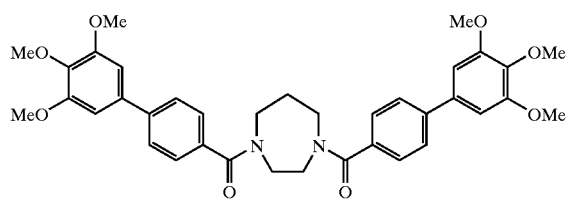

In accordance with the same process as in Example 33, 121 mg (yield: 98%) of crude crystals of the title compound were obtained from 121 mg (0.42 mmol) of 4-(3,4,5-trimethoxyphenyl)benzoic acid synthesized by the process described in Referential Example 16 and 20 mg (0.20 mmol) of homopiperazine. The crude crystals were recrystallized from methylene chloride-hexane, thereby obtaining a colorless crystalline powder.

Melting point: 205–209° C.

$^1$H-NMR (CDCl$_3$) δ:
1.90–2.01(m,2H), 3.40–3.88(m,8H), 3.90(s,6H),
3.93(m,12H), 6.77(s,4H), 7.47(br d,J=7.5 Hz,4H),
7.60(br d,J=7.5 Hz,4H).

Example 70

Preparation of 4,8-bis[4-(3,4,5-trimethoxyphenyl)-benzoyl]-1,4,8-triazabicyclo[4,4,0]decane:

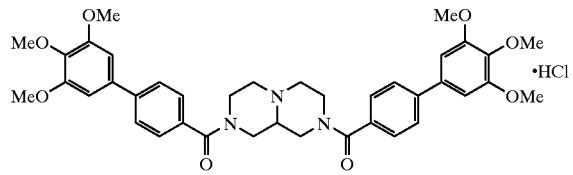

In accordance with the same process as in Example 33, 133 mg (yield: 98%) of 4,8-bis[4-(3,4,5-trimethoxyphenyl)-benzoyl]-1;4,8-triazabicyclo[4,4,0]decane were obtained as a colorless amorphous powder from 121 mg (0.42 mmol) of 4-(3,4,5-trimethoxyphenyl)benzoic acid synthesized by the process described in Referential Example 16 and 28 mg (0.20 mmol) of 1,4,8-triazabicyclo[4,4,0]decane[1].

Added to a solution of 133 mg (0.20 mmol) of the thus-obtained amorphous powder in ethanol (10 ml) was 0.40 ml (0.40 mmol) of 1N hydrochloric acid, and the resultant mixture was concentrated under reduced pressure, thereby obtaining crude crystals of the title compound. The crude crystals were recrystallized from ethanol-diethyl ether, thereby obtaining a colorless crystalline powder.

(1) Gubert, S.; Braojos, C.; Sacristan, A.; Ortiz, J. A. Synthesis, 1991, 318–320.

Melting point: 256° C. (decomposed) (colorless powder).

$^1$H-NMR (DMSO-$d_6$, 120° C.) (no N$^+$H proton of the ammonium salt was observed) δ:

2.60–3.25(m,4H), 3.30–3.48(m,1H), 3.75(s,6H),
3.85(s,12H), 4.01–4.40(m,8H), 6.92(s,4H),
7.47(d,J=8.5 Hz,4H), 7.70(d,J=8.5 Hz,4H).

Example 71

Preparation of 1,4-bis[5-nitro-2-(3,4,5-trimethoxyphenyl)benzoyl]hexahydro-1,4-diazepine:

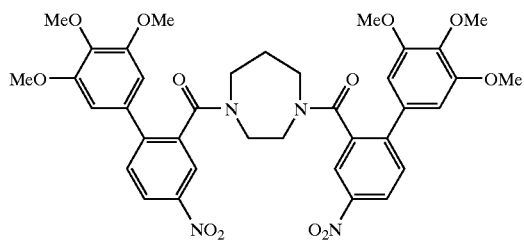

In accordance with the same process as in Example 33, 200 mg (yield: 91%) of crude crystals of the title compound were obtained from 210 mg (0.63 mmol) of 5-nitro-2-(3,4,5-trimethoxyphenyl)benzoic acid and 30 mg (0.30 mmol) of homopiperazine. The crude crystals were recrystallized from ethyl acetate-hexane, thereby obtaining pale yellow needles.

Melting point: 244–245° C.

$^1$H-NMR (DMSO-$d_6$, 120° C.) (mixture of amide rotamers) δ:

1.30–1.51(m,2H), 3.60–3.80(m,8H), 3.73(br s,6H),
3.77(br s,12H), 6.60–6.85(m,4H), 7.51–7.80(m,2H),
8.00–8.15(m,2H), 8.15–8.30(m,2H).

Example 72

Preparation of 1,4-bis[4-methoxy-3-(3,4,5-trimethoxyphenyl)benzoyl]hexahydro-1,4-diazepine:

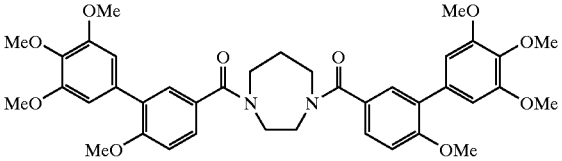

In accordance with the same process as in Example 41, 87 mg (yield: 69%) of the title compound was obtained as a colorless amorphous powder from 126 mg (0.40 mmol) of 4-methoxy-3-(3,4,5-trimethoxyphenyl)-benzoic acid and 18 mg (0.18 mmol) of homopiperazine.

$^1$H-NMR (CDCl$_3$) δ:

1.90–2.00(m,2H), 3.45–3.65(m,4H), 3.70–3.90(m,4H),
3.87(s,12H), 3.89(s,12H), 6.73(s,4H),
6.98(d,J=8.7 Hz,2H), 7.37(d,J=8.7 Hz,2H), 7.38(s,2H).

Example 73

Preparation of 1,4-bis[4-methyl-3-(3,4,5-trimethoxyphenyl)benzoyl]hexahydro-1,4-diazepine:

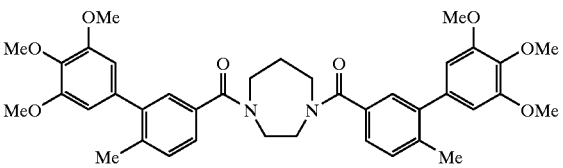

In accordance with the same process as in Example 33, 98 mg (yield: 73%) of the title compound was obtained as a colorless amorphous powder from 127 mg (0.42 mmol) of 4-methyl-3-(3,4,5-trimethoxyphenyl)benzoic acid and 20 mg (0.20 mmol) of homopiperazine.

$^1$H-NMR (DMSO-$d_6$, 120° C.) δ:

1.60–1.80(m,2H), 2.27(s,6H), 3.50–3.65(m,4H),
3.71(br s,4H), 3.74(s,6H), 3.77(s,12H), 6.56(s,4H),
7.18(dd,J=8.0,1.7 Hz,2H), 7.21(d,J=1.7 Hz,2H),
7.27(d,J=8.0 Hz,2H).

Example 74

Preparation of 1,4-bis[4-fluoro-3-(3,4,5-trimethoxyphenyl)benzoyl]hexahydro-1,4-diazepine:

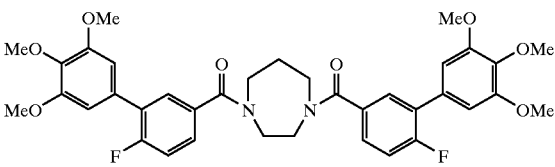

In accordance with the same process as in Example 41, 82 mg (yield: 71%) of the title compound was obtained as a colorless amorphous powder from 115 mg (0.37 mmol) of 4-fluoro-3-(3,4,5-trimethoxyphenyl)benzoic acid and 17 mg (0.17 mmol) of homopiperazine.

$^1$H-NMR (DMSO-$d_6$, 120° C.) δ:
1.70–1.90(m,2H), 3.40–3.70(m,4H), 3.67(s,4H),
3.75(s,6H), 3.80(s,12H), 6.81(s,4H),
7.26(dd,J=10.7,8.5 Hz,2H),
7.37(ddd,J=8.5,5.0,2.2 Hz,2H), 7.49(dd,J=7.6,2.2 Hz,2H).

Example 75

Preparation of 1,4-bis[5-(3,4,5-trimethoxyphenyl)-3-pyridinecarbonyl]hexahydro-1,4-diazepine:

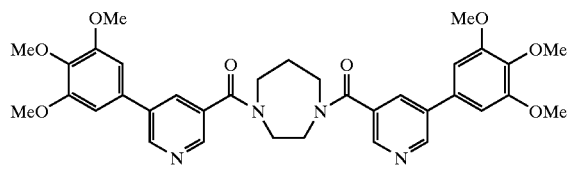

In accordance with the same process as in Example 33, 103 mg (yield: 80%) of crude crystals of the title compound were obtained from 121 mg (0.42 mmol) of 5-(3,4,5-trimethoxyphenyl)-3-pyridinecarboxylic acid and 20 mg (0.20 mmol) of homopiperazine. The crude crystals were recrystallized from ethanol-hexane, thereby obtaining a colorless crystalline powder.

Melting point: 216–217° C.

$^1$H-NMR (DMSO-$d_6$, 120° C.) δ:
1.75–1.90(m,2H), 3.50–3.75(m,8H), 3.75(s,6H),
3.87(s,12H), 6.98(s,4H), 7.99(dd,J=2.0,2.0 Hz,2H),
8.54(d,J=2.0 Hz,2H), 8.92(d,J=2.0 Hz,2H).

Example 76

Preparation of 1,4-bis[5-amino-2-(3,4,5-trimethoxyphenyl)benzoyl]hexahydro-1,4-diazepine:

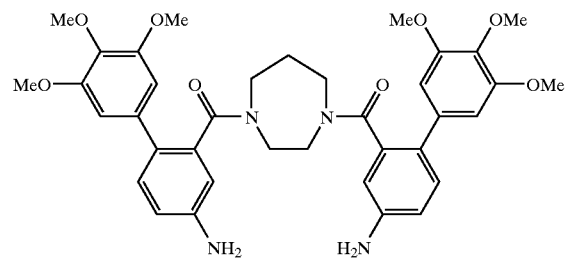

Added to a solution of 39 mg (0.050 mmol) of 1,4-bis[5-nitro-2-(3,4,5-trimethoxy-phenyl)benzoyl]hexahydro-1,4-diazepine synthesized by the process described in Example 71 in acetic acid-ethyl acetate (3:2, 2.5 ml) were 39 mg of 10% palladium on carbon, and the mixture was stirred for 2 hours at room temperature under hydrogen. The catalyst was removed from the reaction mixture by suction filtration through Celite, and the filtrate was concentrated under reduced pressure. A chloroform solution of the residue was washed with a saturated aqueous solution of sodium hydrogencarbonate and a saturated saline solution, dried over anhydrous sodium sulfate and then concentrated under reduced pressure. The resultant crude oil was purified by column chromatography on silica gel to obtain 32 mg (yield: 90%) of the title compound as a pale yellow amorphous powder.

$^1$H-NMR (DMSO-$d_6$, 120° C.) (mixture of amide rotamers) δ:
1.60–1.75(m,2H), 3.60–3.75(m,8H), 3.67(br s,6H),
3.72(br s,12H), 4.93(br s,4H), 6.35–6.45(m,2H),
6.60(br s,4H), 6.60–6.75(m,2H), 7.05–7.15(m,2H).

Test Example 1

Evaluation of Inhibitory Effect on Production of IgE Antibody

A spleen was enucleated from a mouse (Balb/C, male, aged 8 weeks) and shredded in 0.3% BSA/HBSS to prepare single cells by means of a 200-mesh screen. Further, the single cells were hemolyzed by 0.75% ammonium chloride-17 mM Tris solution to prepare a splenocyte suspension ($1 \times 10^7$/ml) using RPMI 1640 medium/25 mM HPES/0.3% BSA. After the suspension was reacted with a mouse anti-mouse Thy-1.2 monoclonal antibody at 4° C. for 1 hour, the reaction mixture was centrifuged, and the sediment cells were suspended again ($1 \times 10^7$/ml, RPMI/HPES/BAS). After the suspension was then reacted with a low-cytotoxic rabbit complement (product of Cedarlane Co.) at 37° C. for 1 hour, killed cells were removed by specific gravity centrifugation using lympholyte M (product of Cedarlane Co.) to obtain a B cell fraction as viably cells.

After B cells ($10^5$/0.2 ml/well) were cultured for a day together with LPS (*E. coli* 026:B6, product of DIFCO Co.) using a 96-well plate, mouse IL-4 (product of Genzyme Co.) was added to conduct culture further for 7 days.

Each test agent was added on the first day of the culture, and the amount of IgE in a culture supernatant was measured by ELISA, thereby calculating out the inhibitory effect of the agent on the production of an IgE antibody. The inhibitory activities of the test agents at a concentration of $10^{-5}$ M are shown in Table 1.

TABLE 1

| Test compound (Example No.) | Inhibitory effect on production of IgE (%) |
| --- | --- |
| 1 | 100 |
| 17 | 100 |
| 19 | 20 |
| 25 | 100 |
| 29 | 100 |
| 32 | 85 |
| 34 | 90 |
| 36 | 100 |
| 41 | 100 |
| 42 | 95 |

INDUSTRIAL APPLICABILITY

The novel diamide compounds (1) according to the present invention have an excellent inhibitory effect on the production of an IgE antibody and are hence useful as agents for preventing and treating various allergic immunological diseases.

What is claimed is:

1. A compound represented by formula (1):

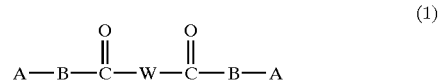

wherein:

A is a phenyl, naphthyl, dihydronaphthyl, indenyl, pyridyl, indolyl, isoindolyl, quinolyl or isoquinolyl group, any of which may be substituted;

B is a group of —CH=CH—, —C≡C—, —(CH=CH)₂—, —CH=CH—C≡C— or —C≡C—CH=CH—, or a divalent residue of benzene, pyridine, pyrimidine or pyrazine, any of which may be substituted; and W is diazepine as shown in the following formula, where n is 3 and X is —CHY¹—CHY²— or n is 2 and X is —CH₂—CHY³—CH₂—

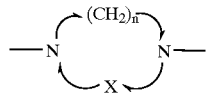

wherein Y¹, Y² and Y³ are each independently selected from the group consisting of:
 a hydrogen atom,
 —COOR¹, wherein R¹ is a hydrogen atom or a lower alkyl group,
 —CON(R²)R³, wherein R² and R³ are each independently selected from the group consisting of a hydrogen atom, a hydroxyl group, and a lower alkyl group,
 —CH₂N(R⁴)R⁵, wherein R⁴ and R⁵ are each independently a hydrogen atom or a lower alkyl group, or R⁴ and R⁵ may form, together with the adjacent nitrogen atom, a heterocyclic ring which may further have an oxygen, nitrogen or sulfur atom, and
 —CH₂—S—R⁶, wherein R⁶ is a lower alkyl, phenyl or pyridyl group;
or a salt thereof, or a hydrate or solvate thereof.

2. The compound according to claim 1, wherein A is a phenyl, naphthyl, dihydronaphthyl, indenyl, pyridyl, indolyl, isoindolyl, quinolyl or isoquinolyl group any of which may have 1–3 substituents independently selected from the group consisting of a hydroxyl group, a halogen atom, a lower alkyl group which may be substituted by 1–3 halogen atoms, a lower alkoxy group, an amino group which may be substituted by one or two lower alkyl groups, and a lower alkylthio group.

3. The compound of claim 1, wherein A is a phenyl or substituted phenyl.

4. The compound of claim 1, wherein A is naphthyl or substituted naphthyl.

5. The compound of claim 1, wherein A is dihydronaphthyl or substituted dihydronaphthyl.

6. The compound of claim 1, wherein A is indenyl or substituted indenyl.

7. The compound of claim 1, wherein A is pyridyl or substituted pyridyl.

8. The compound of claim 1, wherein A is indolyl or substituted indolyl.

9. The compound of claim 1, wherein A is isoindolyl or substituted isoindolyl.

10. The compound of claim 1, wherein A is quinolyl or substituted quinolyl.

11. The compound of claim 1, wherein A is isoquinolyl or substituted isoquinolyl.

12. The compound of claim 1, wherein B is —CH=CH—, which may be substituted.

13. The compound of claim 1, wherein B is —C≡C—.

14. The compound of claim 1, wherein B is a group of —(CH=CH)₂—, which may be substituted.

15. The compound of claim 1, wherein B is —CH=CH—C≡C—, which may be substituted.

16. The compound of claim 1, wherein B is —C≡C—CH=CH—, which may be substituted.

17. The compound of claim 1, wherein B is a divalent residue of benzene, which may be substituted.

18. The compound of claim 1, wherein B is a divalent residue of pyridine, which may be substituted.

19. The compound of claim 1, wherein B is a divalent residue of pyrimidine, which may be substituted.

20. The compound of claim 1, wherein B is a divalent residue of pyrazine, which may be substituted.

21. The compound of claim 1, wherein n is 3 and X is —CHY¹—CHY²—.

22. The compound of claim 1, wherein n is 2 and X is —CH₂—CHY³—CH₂—.

23. A composition comprising the compound according to claim 1 and a pharmaceutically acceptable carrier.

24. The composition according to claim 23 in solid, semi-solid or liquid form.

25. The composition according to claim 23 in the form of a tablet, pill, granule, soft capsule, hard capsule, powder, grain, trituration, emulsion, syrup, pellet or elixir.

26. The composition according to claim 23 in the form of an injection, drop, infusion, ointment, lotion, tonic, spray, inhalation suspension, oil, emulsion or suppository.

27. The composition according to claim 23, wherein said carrier comprises a surfactant, excipient, colorant, smell corrigent, preservative, stabilizer, buffer, suspension stabilizer, or isotonic agent.

28. The composition of claim 23, wherein said compound is an acid-addition salt, a solvate or a hydrate.

29. A method for inhibiting the production of an IgE antibody comprising:
 administering to a subject in need thereof an amount of the compound of claim 1 suitable for inhibiting the production of IgE in said subject.

30. A method for treating an allergic immunological disease comprising administering an effective amount of the compound of claim 1 to a subject in need thereof.

31. The method of claim 30, wherein said allergic immunological disease is selected from the group consisting of asthma, atopic dermatitis, allergic rhinitis, inflammatory large bowel disease and contact dermatitis.

32. The method of claim 30, wherein said effective amount ranges from 0.01–1,000 mg/kg/day.

* * * * *